(12) United States Patent
Yoshino et al.

(10) Patent No.: US 11,304,597 B2
(45) Date of Patent: Apr. 19, 2022

(54) ENDOSCOPE APPARATUS AND OPERATING METHOD OF ENDOSCOPE APPARATUS

(71) Applicant: OLYMPUS CORPORATION, Tokyo (JP)

(72) Inventors: Koichiro Yoshino, Tokyo (JP); Naoya Kuriyama, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/843,013

(22) Filed: Apr. 8, 2020

(65) Prior Publication Data
US 2020/0229688 A1 Jul. 23, 2020

Related U.S. Application Data

(63) Continuation of application No. PCT/JP2017/038385, filed on Oct. 24, 2017.

(51) Int. Cl.
A61B 1/045 (2006.01)
A61B 1/00 (2006.01)
(Continued)

(52) U.S. Cl.
CPC .......... A61B 1/045 (2013.01); A61B 1/00009 (2013.01); H04N 5/23212 (2013.01);
(Continued)

(58) Field of Classification Search
CPC ..... A61B 1/00045; A61B 1/05; A61B 1/0669; A61B 1/07
See application file for complete search history.

(56) References Cited

U.S. PATENT DOCUMENTS

2009/0225201 A1* 9/2009 Abe .......................... G06T 5/50
348/241
2017/0061601 A1 3/2017 Bryll
(Continued)

FOREIGN PATENT DOCUMENTS

JP 2017-049249 A 3/2017
JP 2017-158764 A 9/2017
WO 2016/043107 A1 3/2016

OTHER PUBLICATIONS

International Search Report dated Jan. 16, 2018 issued in International Application No. PCT/JP2017/038385.

Primary Examiner — Dave Czekaj
Assistant Examiner — Berteau Joisil
(74) Attorney, Agent, or Firm — Scully, Scott, Murphy & Presser, P.C.

(57) ABSTRACT

An endoscope apparatus includes a processor. The processor performs controlling a focus position of an objective optical system, acquiring images sequentially captured by an image sensor, and combining the images in N frames thus captured into a depth of field extended image in one frame. The processor controls the focus position such that focus positions at timings when the respective images in N frames are captured differ from each other. The processor combines the images in N frames that have been controlled to receive a constant quantity of light emission of illumination light or the images in N frames that have undergone a correction process to make image brightness constant, into the depth of field extended image.

16 Claims, 18 Drawing Sheets

(51) Int. Cl.
    *H04N 5/232*     (2006.01)
    *A61B 1/05*     (2006.01)
    *A61B 1/06*     (2006.01)
    *A61B 1/07*     (2006.01)

(52) U.S. Cl.
    CPC ............. *A61B 1/00045* (2013.01); *A61B 1/05* (2013.01); *A61B 1/0669* (2013.01); *A61B 1/07* (2013.01)

(56) References Cited

U.S. PATENT DOCUMENTS

| | | |
|---|---|---|
| 2017/0187943 A1 | 6/2017 | Tsuyuki et al. |
| 2019/0107702 A1* | 4/2019 | Gaiduk ............ H04N 5/232133 |
| 2019/0328208 A1* | 10/2019 | Kashima ............ A61B 1/00043 |

* cited by examiner

ENDOSCOPE APPARATUS AND OPERATING METHOD OF ENDOSCOPE APPARATUS

CROSS REFERENCE TO RELATED APPLICATION

This application is a continuation of International Patent Application No. PCT/JP2017/038385, having an international filing date of Oct. 24, 2017, which designated the United States, the entirety of which is incorporated herein by reference.

BACKGROUND

An endoscope apparatus (an endoscope system) is required to have a depth of field as deep as possible so as not to pose a problem for diagnosis and treatment performed by a user. Unfortunately, the endoscope apparatus has recently included an image sensor having a large number of pixels and thus the depth of field has become shallower.

In order to compensate the shallow depth of field in an imaging device, introduction of an extended depth of field (EDOF) technology, which extends the depth of field, is proposed. For example, Japanese Unexamined Patent Application Publication No. 2017-49249 discloses the EDOF technology in a machine vision. According to Japanese Unexamined Patent Application Publication No. 2017-49249, a focus position is changed to show a sine wave, and images are respectively captured at a plurality of peak positions. Then, in-focus regions in the plurality of images are combined to extend the depth of field.

Endoscope apparatus adjusts image brightness as needed to provide a user with images having appropriate brightness for the diagnosis and treatment. For example, an endoscope apparatus has a function to adjust a quantity of light of illumination light emitted to a subject as needed. This function is hereinafter referred to as light adjustment.

SUMMARY

In accordance with one of some embodiments, there is provided an endoscope apparatus comprising a processor, the processor being configured to perform:

controlling a focus position of an objective optical system configured to form an image of reflected light from a subject on an image sensor, the subject reflecting illumination light emitted thereon; acquiring images sequentially captured by the image sensor; and combining the images in N frames thus acquired into a depth of field extended image in one frame, N being an integer of two or more, the processor performs: controlling the focus position such that focus positions at timings when the respective images in N frames are captured differ from each other; and combining the images in N frames that have been controlled to receive a constant quantity of light emission of the illumination light or the images in N frames that have undergone a correction process to make image brightness constant, into a depth of field extended image.

Furthermore, in accordance with one of some embodiments of the present disclosure, the endoscope apparatus includes the focus control section that controls the focus position of the objective optical system configured to form the image of the reflected light from the subject, which reflects illumination light emitted thereon, on the image sensor, the image acquisition section that acquires the images sequentially captured by the image sensor, the image combining section that combines the images in N frames (N is an integer of two or more acquired by the image acquisition section into the depth of field extended image in one frame, and an illumination light control section that controls the illumination light. The focus control section controls the focus position such that the focus positions at the timings when the respective images in N frames are captured differ from each other. The image combining section combines images in a first set of N frames into a first depth of field extended image, and images in a second set of N frames captured after the images in the first set of N frames into a second depth of field extended image. The illumination light control section changes a quantity of light emission of the illumination light in a period between a period when the images in the first set of N frames are captured and a period when the images in the second set of N frames are captured.

In accordance with one of some embodiments, there is provided an operating method of an endoscope apparatus comprising: controlling a focus position of an objective optical system such that focus positions at timings when respective images in N frames are captured differ from each other, N being an integer of two or more; acquiring the images in N frames captured by an image sensor; and combining the images in N frames that have been controlled to receive a constant quantity of light emission of illumination light or the images in N frames that have undergone a correction process to make image brightness constant, into a depth of field extended image in one frame.

DESCRIPTION OF EXEMPLARY EMBODIMENTS

Figure 1:
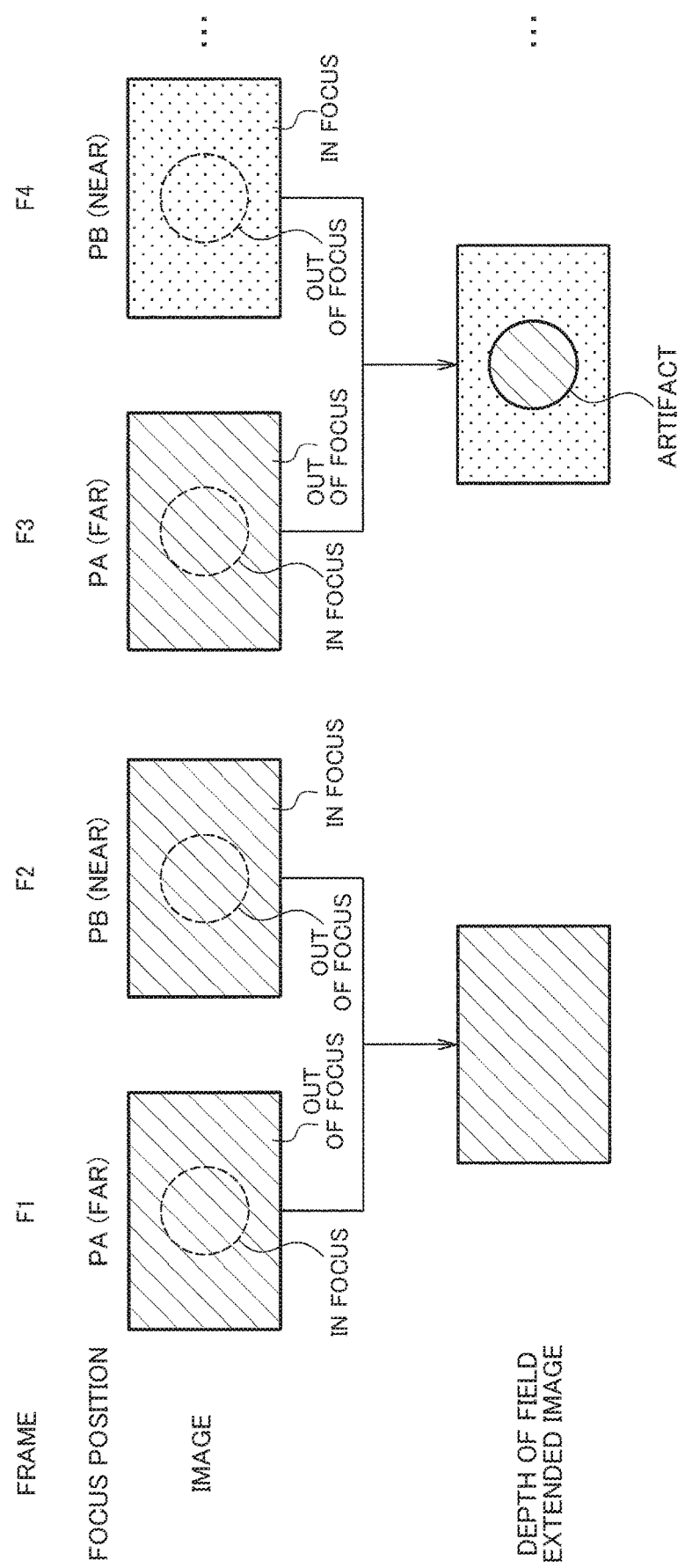
FIG. 1 is a diagram illustrating generation of an artifact when a light adjustment control and an EDOF are combined.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 is a diagram illustrating generation of an artifact when a light adjustment control and an EDOF are combined.

As illustrated in FIG. 1, images in frames F1, F2, F3 and F4 are respectively captured at focus positions PA, PB, PA, and PB. The focus positions PA and PB differ from each other. Assume that an inside of a circle indicated by a dotted line is in focus at the focus position PA and an outside of a circle is in focus at the focus position PB. In this case, the inside of the circle in the image captured at the focus position PA and the outside of the circle in the image captured at the focus position PB are combined to generate a depth of field extended image. The dotted line is only for convenience sake and does not actually exist.

Without a change in quantity of light emission of illumination light (image brightness) the frames F1 and F2, no difference in brightness between the inside and the outside of the circle, serving as a boundary of the combination, is generated and thus no unevenness in brightness is generated in the depth of field extended image. On the other hand, with a change in the quantity of light emission of the illumination light due to a light adjustment in the frames F3 and F4, a difference in brightness between the inside and the outside of the circle, serving as the boundary of the combination, is generated and thus unevenness in brightness is generated in the depth of field extended image. This unevenness in brightness does not actually exist in a subject and may appear as an artifact.

Figure 2:
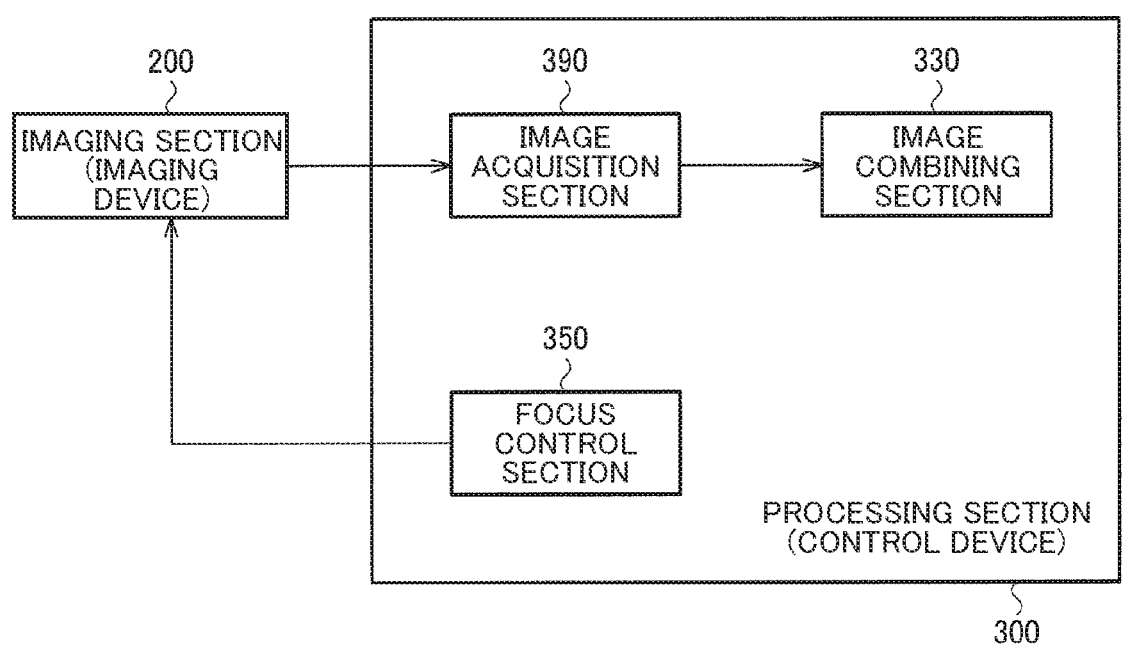
FIG. 2 is a diagram illustrating a configuration example of an endoscope apparatus in accordance with the present embodiment.

FIG. 2 is a configuration example of an endoscope apparatus in accordance with the present embodiment. The endoscope apparatus includes an imaging section 200 (an imaging device) and a processing section 300 (a control device).

The imaging section 200 includes an objective optical system (an optical device) that forms an image of reflected light from the subject, which reflects the illumination light emitted thereon, on an image sensor, and the image sensor. The processing section 300 includes a focus control section 350 that controls the focus position of the objective optical system, an image acquisition section 390 that acquires images sequentially captured by the image sensor, and an image combining section 330 that combines images in N frames (N is an integer of two or more) acquired by the image acquisition section 390 into a depth of field extended image in one frame. The focus control section 350 controls the focus position such that focus positions at timings when the respective images in N frames are captured differ from each other. The image combining section 330 combines the images in N frames that have been controlled to receive a constant quantity of light emission of the illumination light or the images in N frames that have undergone a correction process to make image brightness constant, into the depth of field extended image.

For example, as will be described later referring to FIG. 5 or the like, the focus control section 350 sets the focus position to focus positions PA and PB that differ from each other at timings when respective images IA1 and IA2 are captured. The image combining section 330 combines the images IA1 and IA2 in two frames (N=2) into a depth of field extended image EIA in one frame. Alternatively, as will be described later referring to FIG. 9, the focus control section 350 sets the focus position to focus positions PE, PF, and PG that differ from each other. The image combining section 330 combines images in three frames (N=3) captured at the focus positions PE, PF, and PG into the depth of field extended image in one frame. N is not limited to two or three.

As will be described later referring to FIG. 10, the respective quantities of light emission of the illumination light when the images (e.g., images IA1 and IA2) in N frames are captured are controlled to be equal. The quantity of light emission when images (e.g., the images IA1 and IA2) in one set of N frames are captured may differ from the quantity of light emission when images (e.g., images IB1 and IB2) in another set of N frames are captured. Alternatively, as will be described later referring to FIG. 17, the correction process for correcting the image brightness by image processing may be performed to equalize the brightness of the respective images in N frames. The image brightness is represented by a luminance value or a G pixel value, for example, and is represented by a pixel value of an image obtained by applying a filter process (a smoothing process a luminance image or a G image, for example. That is, the correction process is performed to equalize the brightness of each local region (e.g., each pixel) in the image with all corresponding local regions in the images in N frames.

Figure 3:
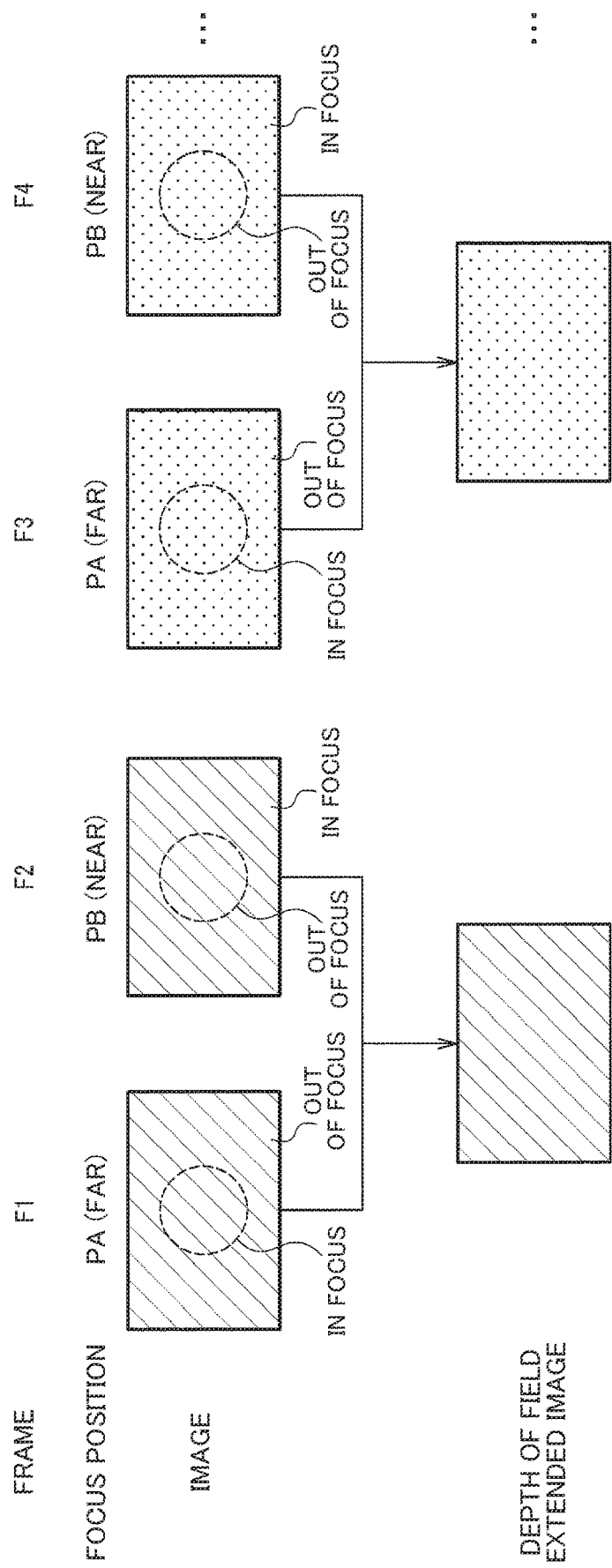
FIG. 3 is a diagram illustrating an operation of the endoscope apparatus in accordance the present embodiment.

As a result, in the present embodiment, the images in N frames that have been controlled to receive the constant quantity of light emission of the illumination light or the images in N frames that have undergone the correction process to make the brightness constant are combined into the depth of field extended image, and thus generation of an artifact in the depth of field extended image can be suppressed. For example, as illustrated in FIG. 3, the quantity of light emission of the illumination light or the image brightness is equal in images in frames F1 and F2 that are to be combined into a depth of field extended image in one frame. Similarly, the quantity of light emission of the illumination light or the image brightness is equal in images in frames F3 and F4 that are to be combined into a depth of field extended image in one frame. Consequently, no difference in brightness is generated between the inside and the outside of the circle (the dotted line), serving as the boundary of the combination, and thus no unevenness in brightness is generated in the depth of field extended image.

The focus position is a position in focus on a subject side (a position of an in-focus plane or a position of an intersection of the in-focus plane and an optical axis). Specifically, the focus position is represented by a distance from a reference position of the imaging section (e.g., a position of the image sensor or a distal end of an objective lens) to the position in focus on the subject side (the position of the in-focus plane). The focus position is adjusted by moving a focus lens (a lens used for focus adjustment) in an objective lens system. That is, the focus position and a position of the focus lens correspond to each other.

The depth of field extended image is an image whose depth of field is artificially extended based on a plurality of images having different focus positions. For example, a best focused image of the images in N frames is selected in each local region (e.g., each pixel) of the image, and used to form the depth of field extended image. The images in N frames that are to be combined into the depth of field extended image in one frame are images sequentially captured (in consecutive N frames) by the image sensor.

The quantity of light emission of the illumination light is a total quantity of light emission in one exposure period of the image sensor. The total quantity of light emission corresponds to a value found by integrating time changes in the quantity of light emission with respect to time in the exposure period. The total quantity of light emission is controlled by a light emission period or a quantity of light emission per unit time. Alternatively, in a case of pulse light emission, the total quantity of light emission is controlled by a number of pulses or a quantity of light emission of each pulse.

Figure 4:
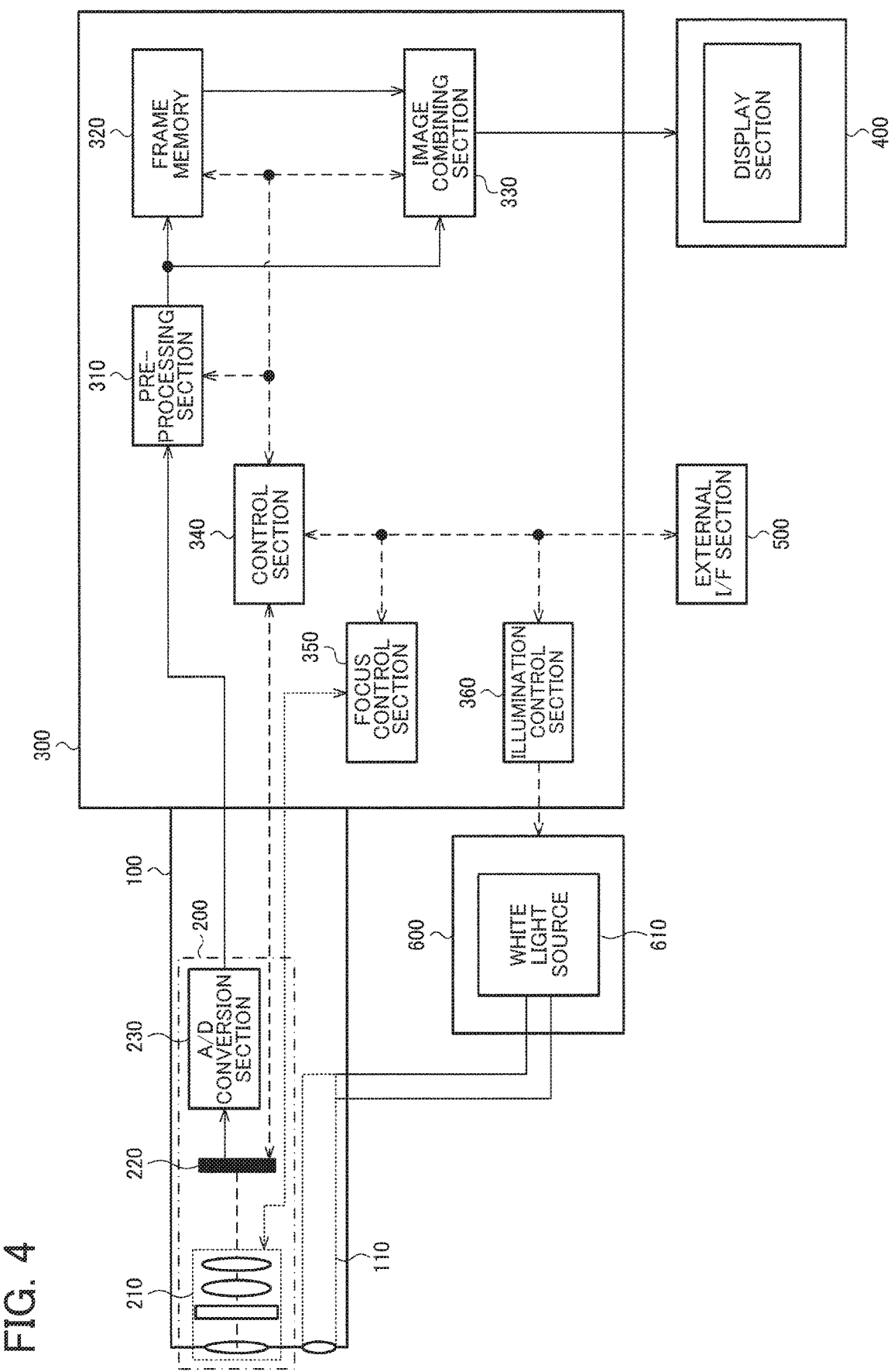
FIG. 4 is a diagram illustrating a detailed configuration example of the endoscope apparatus.

Furthermore, in accordance with the present embodiment, when the image combining section 330 combines the images in N frames that have been controlled to receive the constant quantity of light emission of the illumination light into the depth of field extended image, the endoscope apparatus includes an illumination control section (an illumination control section 360 in FIG. 4). The illumination control section controls the illumination light to adjust the brightness of the depth of field extended image, and also maintains the quantity of light emission constant when the images in N frames are captured.

Specifically, the illumination control section controls the illumination light (the quantity of light emission) to make the brightness of the depth of field extended image appropriate. For example, the illumination control section controls the illumination light so as to maintain the brightness of the depth of field extended image constant, or to reduce a change in the brightness of the depth of field extended image (compared with a case without a light adjustment). Furthermore, the illumination control section maintains (does not change) the quantity of light emission of the illumination light when the images in N frames are captured, and changes the quantity of light emission of the illumination light after capturing the images in N frames is finished and before capturing the images in a subsequent set of N frames is started. This is how the quantity of light emission is made constant when the images in N frames are captured.

Figure 5:
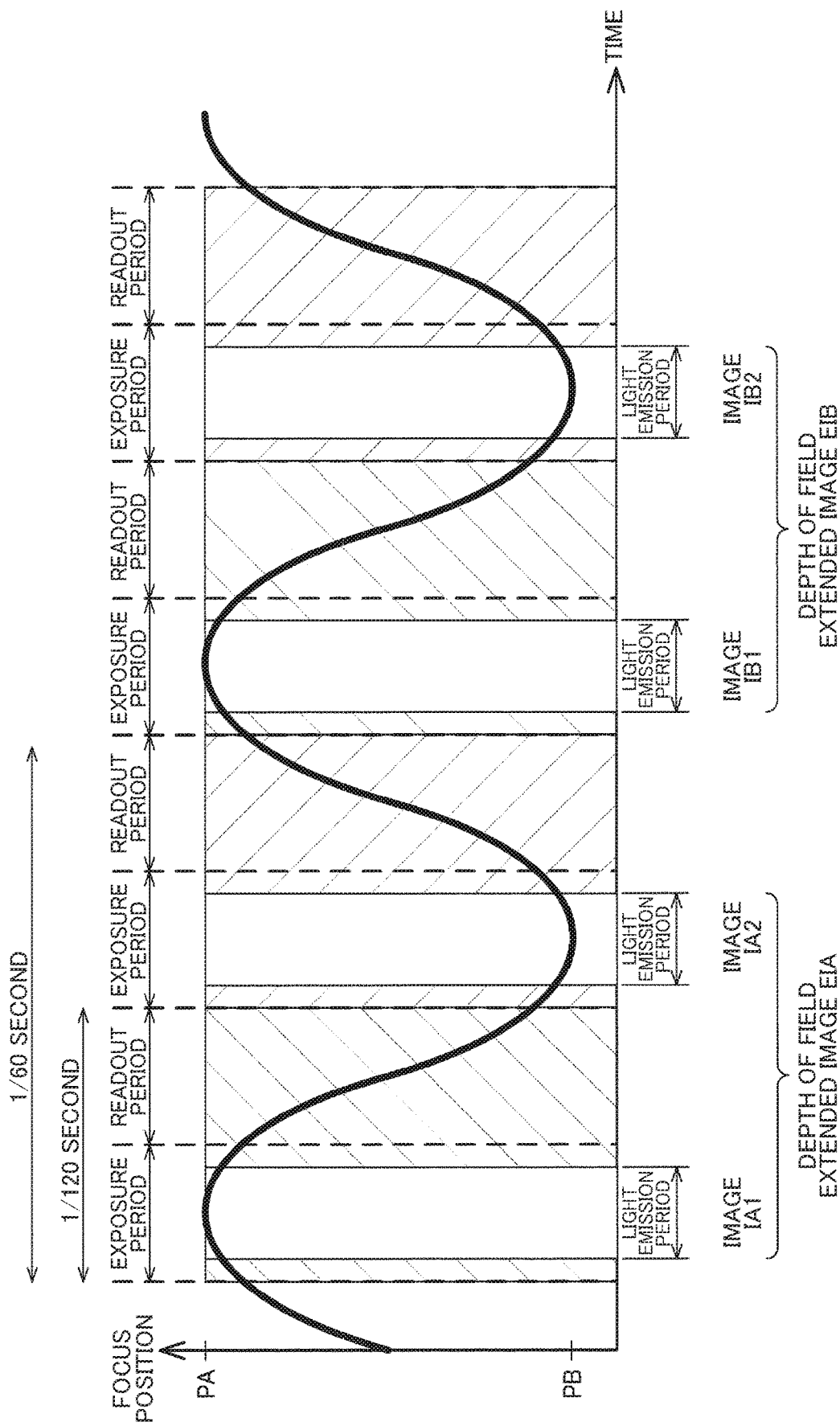
FIG. 5 is a graph illustrating an operation of the endoscope apparatus of the detailed configuration example.

For example, as illustrated in FIG. 5 or the like, the image sensor performs imaging at a frame rate of N times a frame rate of the depth of field extended image. In this case, the images in N frames to be combined into the depth of field extended image do not overlap the images in N frames to be combined into the subsequent depth of field extended image. For example, the quantity of light emission of the illumination light for the respective images in N frames can be made constant in all sets of N frames. However, the present disclosure is not limited to this, and the quantity of light emission of the illumination light for the respective images in N frames may not be constant in some sets of N frames. That is, it is only needed that the images in N frames that are controlled to receive the constant quantity of light emission of the illumination light exist. For example, the images in N frames that have received different quantities of light emission of the illumination light may undergo the correction process, described later, to make the image brightness constant. Furthermore, the frame rate of imaging by the image sensor may not be N times the frame rate of the depth of field extended image.

As a result, in the present embodiment, the illumination control section makes the quantity of light emission constant when the images in N frames are captured, and thus the image combining section 330 can combine the images in N frames that have been controlled to receive the constant quantity of light emission of the illumination light into the depth of field extended image. This configuration can suppress generation of an artifact in the depth of field extended image.

Furthermore, in accordance with the present embodiment, the illumination control section performs a control for emitting the illumination light in a light emission period including a stop timing of the focus position.

For example, as will be described later referring to FIG. 12, the stop timing of the focus position e.g., a timing ta1) coincides with a center of a light emission period (TLA1). The center of the light emission period is a timing when one-half of the light emission period has elapsed since the light emission period started.

As a result, in the present embodiment, the illumination light is emitted in the light emission period including the stop timing of the focus position and thus a change in the focus position in the light emission period can be made small. The light emission period is approximately an imaging period in the endoscope apparatus. Although the change in the focus position in the light emission period may deteriorate an image quality, deterioration in image quality can be suppressed in accordance with the present embodiment.

Furthermore, in accordance with the present embodiment, the focus control section 350 reciprocates the focus position between a first focus position and a second focus position that differs from the first focus position. The illumination control section performs a control for emitting the illumination light in a first light emission period including a timing when the focus position is at the first focus position and in a second light emission period including a timing when the focus position is at the second focus position. The image combining section 330 combines the images in N frames including the image captured in the first light emission period and the image captured in the second light emission period into the depth of field extended image.

Figure 12:
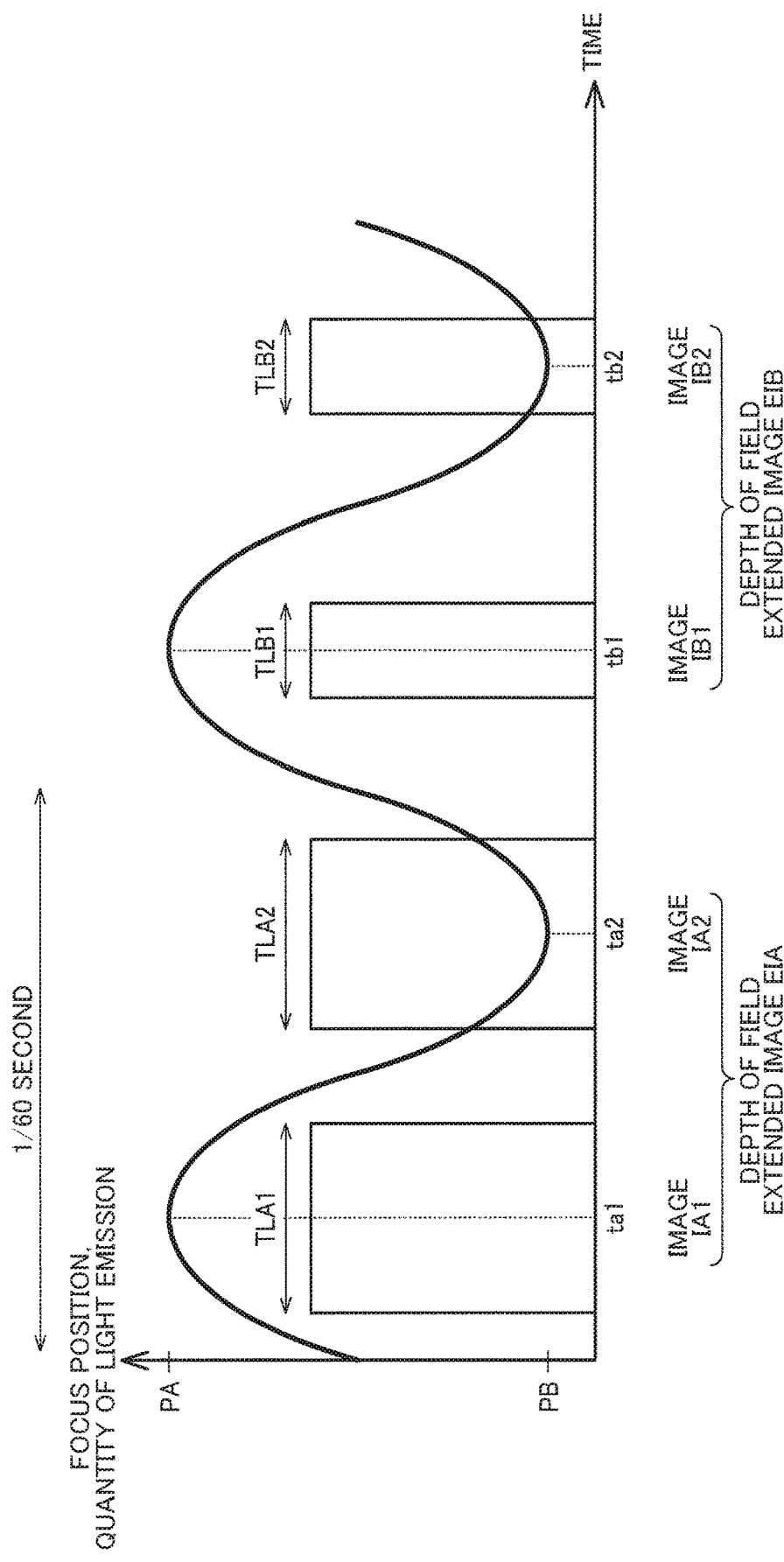
FIG. 12 is a graph illustrating a synchronous control between the focus position and a light emitting timing.

For example, in an example illustrated in FIG. 12, the first focus position is the focus position PA, the first light emission period is the light emission period TLA1, the second focus position is the focus position PB, and the second light emission period is a light emission period TLA2. An image IA1 captured in the first light emission period TLA1 and an image IA2 captured in the second light emission period TLA2 are combined into a depth of field extended image EIA. Furthermore, an additional image may be captured at another different focus position and the images including the additional image in three or more frames may be combined into the depth of field extended image.

As a result, in the present embodiment, the first focus position and the second focus position are turning points of the reciprocation and thus the timings when the focus position is at the first focus position and the second focus position are the stop timings of the focus position. Accordingly, the first light emission period and the second light emission period are the light emission periods each including the stop timing of the focus position. In addition, reciprocating the focus position between the first focus position and the second focus position allows sequentially acquiring the images captured at the first focus position and the second focus position. Consequently, these images can be acquired as a video. Then, sequentially combining the images into the depth of field extended images allows presentation of the video including the depth of field extended images to a user. Furthermore, imaging at the first focus position and the second focus position serving as the turning points of the reciprocation allows imaging at two focus positions that are separated the most and consequently efficiently extending the depth. In addition, as will be described later referring to FIG. 5, the depth of field at the first focus position and the depth of field at the second focus position are preferably continuous. The two continuous depths of filed allows more efficient extension of the depth when the images captured at the first focus position and the second focus position are combined.

Furthermore, in accordance with the present embodiment, the image sensor may capture the image by a rolling shutter system. The illumination control section performs a control for emitting the illumination light in a whole-pixel exposure period in which all lines (all scanning lines, all pixels) in an effective pixel region of the image sensor are in an exposure state.

For example, as will be described later referring to FIG. 13, a center of the whole-pixel exposure period coincides with a center of the light emission period. The center of the whole-pixel exposure period is a timing when one-half of the whole-pixel exposure period has elapsed since the whole-pixel exposure period started.

As a result, in the present embodiment, the subject can be imaged in the whole-pixel exposure period in which all the lines in the effective pixel region of the image sensor are in the exposure state. This configuration can prevent a rolling shutter distortion. The rolling shutter distortion is a distortion in an image generated when a moving subject is captured by the rolling shutter system.

The effective pixel region is a region of pixels used as image data (or displayed as a display image) out of a pixel array of the image sensor. The effective pixel region may be entire or a part of the pixel array of the image sensor. For example, the pixel array of the image sensor may include a dummy pixel that is not used as the image data (or not displayed as the display image). In such a case, the effective pixel region is a region of effective pixels left after removing the dummy pixel from the pixel array.

Furthermore, in accordance with the present embodiment, the illumination control section controls a length of the light emission period of the illumination light to control the total quantity of light emission in image capturing.

For example, as will be described later referring to FIG. 10, the illumination control section changes the length of the light emission period (the length of the light emission period in one exposure period) without changing the quantity of light emission per unit time to control the total quantity of light emission. In this case, the length of light emission period (TLA) is constant when the images (e.g., images IA1 and IA2) in N frames to be combined into the depth of field extended image in one frame are captured. The illumination control section may control both the length of the light emission period and the quantity of light emission per unit time to control the total quantity of light emission.

As a result, in the present embodiment, controlling the length of the light emission period of the illumination light allows controlling the total quantity of light emission in image capturing. That is, the total quantity of light emission can be increased by extending the light emission period of the illumination light. In addition, with a control of the length of the light emission period of the illumination light, the total quantity of light emission can be controlled to be constant when the images in N frames to be combined into the depth of field extended image in one frame are captured.

Furthermore, in accordance with the present embodiment, the illumination control section may control the quantity of light emission of the illumination light per unit time to control the total quantity of light emission in image capturing.

For example, as will be described later referring to FIG. 11, the illumination control section changes the quantity of light emission per unit time without changing the length of the light emission period to control the total quantity of light emission. In this case, a quantity of light emission (LAA) per unit time is constant when the images (e.g., images IA1 and IA2) in N frames to be combined into the depth of field extended image in one frame are captured.

As a result, in the present embodiment, with a control of the quantity of light emission of the illumination light per unit time, the total quantity of light emission in image capturing can be controlled. That is, the total quantity of light emission can be increased by increasing the quantity of light emission per unit time. In addition, with a control of the quantity of light emission per unit time, the total quantity of light emission can be controlled to be constant when the images in N frames to be combined into the depth of field extended image in one frame are captured.

Furthermore, in accordance with the present embodiment, the illumination control section performs a control for emitting the illumination light in the light emission period when a center of the exposure period of the image sensor coincides with the center of the light emission period.

The exposure period is repeated in a given cycle in video shooting. Making the center of the exposure period coincide with the center of the light emission period allows simplification of a synchronous control between the focus position, which changes periodically, and the light emission period. For example, a cycle of the exposure period and a cycle of a change in the focus position are set to an integer ratio to make a given phase of the change in the focus position (e.g., the stop timing of the focus position) coincide with the center of the exposure period. Then, the center of the exposure period is made to coincide with the center of the light emission period to capture the image at the given phase of the change in the focus position. For example, when the length of the light emission period is changed, the center of the exposure period is made to coincide with the center of the light emission period so that the relationship between the phase of the change in the focus position and the center of the light emission period is maintained.

The exposure period is a period when a pixel of the image sensor is in a state capable of storing electric charges (exposure state). As for a global shutter system, as will be described later referring to FIG. 5, exposure is simultaneously started for the entire pixels (all the lines in the effective pixel region) of the image sensor and is simultaneously stopped. In this case, the exposure period is a period from a start to an end of the exposure. The center of the exposure period is a timing when one-half of the exposure period has elapsed since the exposure period started.

Furthermore, in accordance with the present embodiment, the illumination control section causes the illumination light to he emitted by pulse light emission a plurality of times in the exposure period of the image sensor. At this time, a gravity center of a total quantity of light emission of the pulse light emission coincides with the stop timing of the focus position.

Specifically, a total quantity of light emission of the pulse light emission in a period before the stop timing of the focus position out of the exposure period may coincide with a total quantity of light emission of the pulse light emission in a period after the stop timing of the focus position out of the exposure period. That is, it is only needed that an integrated value of quantities of light emission of pulses before the stop timing of the focus position is equal to an integrated value of quantities of light emission of pulses after the stop tinting of the focus position.

For example, as will be described later referring to FIG. 15, assuming that the quantity of light emission is equal in respective pulses and an interval between the light emission of the respective pulses is constant, the number of pulses (twice) before the stop timing of the focus position (e.g., a timing ta1) is equal to the number of pulses (twice) after the stop timing of the focus position.

As a result, in the present embodiment, the image can also be captured at the stop timing of the focus position, even when the illumination light is emitted by pulse light emission. That is, assuming that a period from a start to an end of the pulse light emission is an image capturing period, an image can be captured in the image capturing period including the stop timing of the focus position.

Furthermore, in accordance with the present embodiment, the image combining section 330 combines images in a first set of N frames into a first depth of field extended image and images in a second set of N frames captured after the images in the first set of N frames into a second depth of field extended image. The illumination control section changes the quantity of light emission of the illumination light in a period between a period when the images in the first set of N frames are captured and a period when the images in the second set of N frames are captured.

Figure 10:
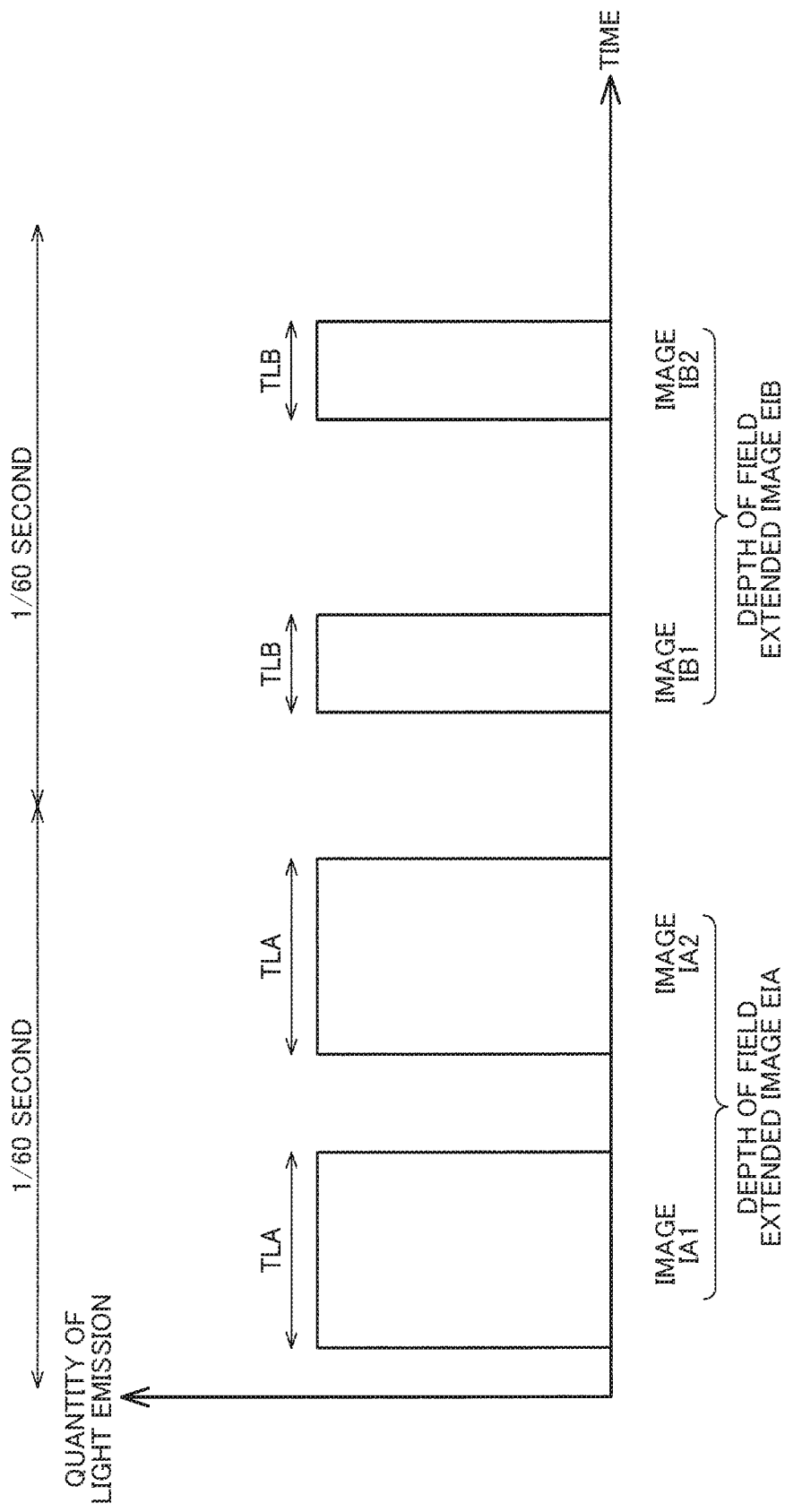
FIG. 10 is a graph of a first example of a control method of a quantity of light emission.

For example, in an example illustrated in FIG. 10, the images in the first set of N frames are images IA1 and IA2 and the first depth of field extended image is an image EIA, and the images in the second set of N frames are images IB1 and IB2 and the second depth of field extended image is an image EIB. The quantity of light emission of the illumination light is changed after the exposure period (or the light emission period) of the image IA2 ends and before the exposure period (or the light emission period) of the image IB1 starts. In the example illustrated in FIG. 10, the light emission period is changed from a period TLA to a period TLB. Alternatively, as illustrated in FIG. 11, the quantity of light emission per unit time may be changed from a quantity LAA to a quantity LAB.

As a result, in the present embodiment, the quantity of light emission of the illumination light is changed in the period between the period when the images in the first set of N frames are captured and the period when the images in the second set of N frames are captured. Thus, the quantity of light emission when the images in the first set of N frames are captured can be maintained at a first quantity of light emission and the quantity of light emission when the images in the second set of N frames are captured can be maintained at a second quantity of light emission. This configuration allows maintaining the quantity of light emission of the illumination light constant when the images in N frames to be combined into the depth of field extended image in one frame are captured.

Furthermore, in accordance with the present embodiment, when the image combining section 330 combines the images in N frames that have undergone the correction process to make the brightness constant, into the depth of field extended image, the endoscope apparatus includes the illumination control section that performs a control of the illumination light to adjust the brightness of the images captured by the image sensor. The image combining section performs the correction process to make the brightness of the respective images in N frames constant, and combines the images in N frames that have undergone the correction process into the depth of field extended image.

When the illumination control section controls the illumination light, the brightness of the respective images in N frames to be combined into the depth of field extended image in one frame may vary. In accordance with the present embodiment, the correction process is performed to make the brightness of the respective images in N frames constant and thus to make the brightness of the images in N frames to be combined into the depth of field extended image in one frame constant. This configuration can suppress generation of an artifact (unevenness in brightness) in the depth of field extended image.

The example illustrated in FIG. 5 or the like is described assuming that the image sensor captures the images at the frame rate (e.g., 120 frames per second [fps] when N=2) of N times the frame rate (e.g., 60 fps) of the depth of field extended image. However, the present disclosure is not limited to this. For example, the image sensor may capture the images at the frame rate equal to the frame rate of the depth of field extended image. In this case, the images in N frames to be combined into the depth of field extended image overlap each other. For example, in the example illustrated in FIG. 5, the images IA1 and IA2 are combined into a first depth of field extended image, the images IA2 and IB1 are combined into a second depth of field extended image, and the images IB1 and IB2 are combined into a third depth of field extended image. In this case, the depth of field extended images of the frame rate equal to the frame rate (120 fps) of image capturing are obtained. For example, when the light adjustment is performed between the images IA2 and IB1, the images having different brightness are combined into the second depth of field extended image. In this case, as described above, the correction process for correcting the image brightness by the image processing is performed to equalize the brightness of the images IA2 and IB1. Then, the resultant images are combined into the second depth of field extended image.

The endoscope apparatus in accordance with the present embodiment may have the configuration described below. The endoscope apparatus in accordance with the present embodiment includes a memory that stores information (e.g., a program and various types of data), and a processor (a processor including hardware) that operates based on the information stored in the memory. The processor performs a focus control process that controls the focus position of the objective optical system, an image acquisition process that acquires the images sequentially captured by the image sensor, and an image combining process that combines the images in N frames into the depth of field extended image in one frame. The focus control process is for controlling the focus position such that the focus positions at timings when the respective images in N frames are captured differ from each other. The image combining process is for combining the images in N frames that have been controlled to receive the constant quantity of light emission of the illumination light or the images in N frames that have undergone the correction process to make the brightness constant, into the depth of field extended image.

For example, the processor may have functions of sections each implemented by individual hardware, or the functions of sections each implemented by integrated hardware. For example, the processor may include hardware, and the hardware may include at least one of a circuit that processes a digital signal and a circuit that processes an analog signal. For example, the processor may include one or more circuit devices (e.g., an integrated circuit [IC]) mounted on a circuit board, or one or more circuit elements (e.g., a resistor or a capacitor). The processor may be a central processing unit (CPU), for example. Note that the processor is not limited to the CPU, but various other processors such as a graphics processing unit (GPU) or a digital signal processor (DSP) may also be used. The processor may be a hardware circuit that includes an application specific integrated circuit (ASIC). The processor may include an amplifier circuit, a filter circuit, or the like that processes an analog signal. The memory may be a semiconductor memory such as a static random-access memory (SRAM) or a dynamic random-access memory (DRAM), or may be a register. The memory may be a magnetic storage device such as a hard disk drive, or may be an optical storage device such as an optical disc device. For example, the memory may store a computer-readable instruction. A function of each section of the endoscope apparatus is implemented as a process when the processor executes the instruction. The instruction may be an instruction set that is included in a program, or may be an instruction that instructs the hardware circuit included in the processor to operate. The endoscope apparatus includes the sections (the image acquisition section 390, the image combining section 330, and the focus control section 350) in the processing section 300, as illustrated in FIG. 2. for example. Alternatively, the endoscope apparatus includes the sections (the image combining section 330, the focus control section 350, a preprocessing section 310, a control section 340, and the illumination control section 360) in the processing section 300, as illustrated in FIG. 4.

Each of the sections of the endoscope apparatus in accordance with the present embodiment may be implemented as a module of a program that operates on the processor. For example, the focus control section 350 is implemented as a focus control module that controls the focus position in the objective optical system. Similarly, the image acquisition section 390 is implemented as an image acquisition module that acquires the images sequentially captured by the image sensor. The image combining section 330 is implemented as an image combining module that combines the images in N frames into the depth of field extended image in one frame. The focus control module controls the focus position such that the focus positions at the timings when the respective images in N frames are captured differ from each other. The image combining module combines the images in N frames that have been controlled to receive the constant quantity of light emission of the illumination light or the images in N frames that have undergone the correction process to make the brightness constant, into the depth of field extended image.

Furthermore, the program implementing the processes performed by the sections of the endoscope apparatus in accordance with the present embodiment can be stored, for example, in a computer-readable information storage medium. The information storage medium can be implemented by an optical disk, a memory card, a hard disc drive (HDD), or a semiconductor memory (a read-only memory [ROM]), for example. The endoscope apparatus (the processing section 300) performs various processes in accordance with the present embodiment based on the program (the data) stored in the information storage medium. Thus, the information storage medium stores the program causing a computer (a device including an input device, a processing section, a storage section, and an output section) to function as components of the endoscope apparatus in accordance with the present embodiment (i.e., the program causing the computer to execute the processes of the components).

2. Detailed Configuration Example

FIG. 4 is a detailed configuration example of the endoscope apparatus. The endoscope apparatus includes an insertion section 100 (a scope), the processing section 300 (a control device or a processing device), a display section 400 (a display device), an external I/F section 500 (an interface, an operation section, or an operation device), and an illumination section 600 (an illumination device or a light source). The endoscope apparatus may include a flexible scope used for a digestive tract or the like and a rigid scope used for a laparoscope or the like, for example.

The insertion section 100 is inserted into the body. The insertion section 100 includes a light guide section 110 (a light guide) and the imaging section 200 (an imaging device).

The light guide section 110 guides light emitted from the illumination section 600 to a distal end of the insertion section 100. The illumination section 600, for example, includes a white light source 610 (e.g., a light-emitting diode [LED] or a xenon lamp), and emits the illumination light of white light. The illumination light is not limited to the white light, and illumination light of various bands used for the endoscope apparatus may be adopted.

The imaging section 200 forms an image of reflected light from the subject to capture an image of the subject. The imaging section 200 includes an objective lens system 210 (the objective lens), an image sensor 220, and an A/D conversion section 230 (an A/D conversion circuit).

The objective lens system 210 forms an image from the reflected light from the subject, which reflects light emitted thereon from the light guide section 110, as a subject image. The focus position of the objective lens system 210 is variable and is controlled by the focus control section 350 described later.

The image sensor 220 photoelectrically converts the subject image formed into the image with the objective lens system 210 to capture (generate) the image. The A/D conversion section 230 converts analog signals sequentially output from the image sensor 220 into digital images and sequentially outputs the digital images to the preprocessing section 310. Specifically, the image sensor 220 shoots a video of the subject. The images in respective frames of the video are subjected to the A/D conversion to be output as digital images to the preprocessing section 310.

The processing section 300 performs signal processing including the image processing and a control of the endoscope apparatus. The processing section 300 includes the preprocessing section 310 (a preprocessing circuit), a frame memory section 320 (a memory), the image combining section 330 (an image combining circuit), the control section 340 (a control circuit or a controller), the focus control section 350 (a focus position control section, a focus control circuit, or a focus controller), and the illumination control section 360 (an illumination control circuit or an illumination controller).

The preprocessing section 310 performs the image processing including a white balance process and an interpolation process (a demosaicing process) on the images sequentially output from the A/D conversion section 230, and sequentially outputs the resultant images to the frame memory section 320 and the image combining section 330. The preprocessing section 310 in FIG. 4 corresponds to the image acquisition section 390 in FIG. 2.

The frame memory section 320 stores at least one frame (one or more frames) of the image output from the preprocessing section 310. The stored image is output to the image combining section 330. Assuming that the number of frames of the images to be combined into the depth of field extended image is N, and the number of frames stored in the frame memory section 320 is N−1.

The image combining section 330 combines the image in one or more frames stored in the frame memory section 320 and the image output from the preprocessing section 310 into the depth of field extended image in one frame, and outputs the depth of field extended image. That is, the image combining section 330 selects a local region including a best focused image of the images in N frames for each local region in the depth of field extended image to generate the depth of field extended image in one frame. The image combining section 330 sequentially generates the depth of field extended images from the frames in the video captured by the image sensor 220 to produce a video including the depth of field extended images as frame images.

The control section 340 is bidirectionally connected to the image sensor 220, the preprocessing section 310, the frame memory section 320, the image combining section 330, the focus control section 350, and the illumination control section 360 to control these sections. For example, the control section 340 controls synchronization of the exposure period of the image sensor 220, the focus position (a focus control signal output from the focus control section 350), and the light emission period (an illumination control signal output from the illumination control section 360). Details of a synchronous control will be described later.

The focus control section 350 outputs the focus control signal for controlling the focus position of the objective lens system 210. Specifically, the focus control section 350 moves the focus position of the objective lens system 210 such that the focus position reciprocates in a predetermined range of the focus position in a predetermined cycle. Details of a focus position control will be described later. The images are captured at a plurality of timings (N frames) at different focus positions, and the images in N frames are combined into one frame by the image combining section 330. As a result, the depth of field extended image having the extended depth of field is acquired.

The illumination control section 360 outputs the illumination control signal for controlling the quantity of light emission emitted from the illumination section 600. Specifically, the illumination control section 360 controls the light emission period and the quantity of light emission per unit time to control the total quantity of light emission in one exposure period of the image sensor 220. In accordance with the present embodiment, the illumination control section 360 does not change the quantity of light emission in each exposure period (makes the quantity of light emission equal in the respective exposure periods) when the images in N frames to be combined into the depth of field extended image are captured. Details of a control of the quantity of light emission will be described later.

The display section 400 sequentially displays the depth of field extended images output from the image combining section 330. That is, the display section 400 displays the video including the depth of field extended images as the frame images. The display section 400 may be a liquid crystal display or an electroluminescence (EL) display, for example.

The external I/F section 500 is an interface used for input to the endoscope apparatus by the user, for example. That is, the external I/F section 500 is, for example, an interface used to operate the endoscope apparatus or an interface used for operation setting of the endoscope apparatus. For example, the external I/F section 500 includes an adjustment button for adjusting a parameter for the image processing.

An operation of the endoscope apparatus in accordance with the present embodiment is described below. FIG. 5 is a graph illustrating the operation of the endoscope apparatus of the detailed configuration example.

As illustrated in FIG. 5, the image sensor 220 performs imaging at 120 fps. The exposure period is a period when the image sensor 220 is in the exposure state (the state that a pixel stores electric charges converted by photoelectric conversion). A readout period is a period when the electric charges stored in the pixel of the image sensor 220 are read out as a signal (an image). The illumination control section 360 causes the illumination section 600 to emit light in the exposure period. That is, the light emission period is in the exposure period, and the illumination control section 360 causes the illumination section 600 to emit light in the light emission period. The focus control section 350 preferably stops the focus position in the light emission period, and changes the focus position in a period other than the light emission period. That is, the focus control section 350 reciprocates the focus position between the focus position PA (e.g., a focus position on a far point side) and the focus position PB (e.g., a focus position on a near point side). The focus position stops at each of the focus position PA and the focus position PB at a certain timing, and the light emission period includes this timing. The light emission period is not limited to the period including the timing when the focus position stops. It is only needed that a change in the focus position in the light emission period is relatively smaller than a change in the focus position in the period other than the light emission period.

The operation described above allows sequentially capturing the image IA1 at the focus position PA, the image IA2 at the focus position PB, the image IB1 at the focus position PA, and the image IB2 at the focus position PB.

The depth of field at the focus position PA is preferably continuous to the depth of field at the focus position PB. For example, when the focus position PA is on the far point side of the focus position PB, an end of the depth of field on the near point side at the focus position PA preferably meets an end of the depth of field on the far point side at the focus position PB. The depth of field at the focus position PA may partially overlap the depth of field at the focus position PB. For example, one-half or smaller regions of the depths of field at the focus position PA and the focus position PB may overlap each other. Preferably, one-quarter or smaller regions of the depths of field at the focus position PA and the focus position PB may overlap each other.

The image combining section 330 combines the images IA1 and IA2 to output the depth of field extended image EIA, and combines the images IB1 and IB2 to Output the depth of field extended image EIB. The respective total quantities of light emission when the images IA1 and IB1 are captured may differ from each other, since the brightness of the depth of field extended images is adjusted as appropriate to be most suitable for observation. On the other hand, the respective total quantities of light emission when the images IA1 and IA2 are captured are maintained constant, and the respective total quantities of light emission when the images IB1 and IB2 are captured are maintained constant. This configuration can suppress generation of an artifact at a time of image combination.

3. Focus Position Control

Figure 6:
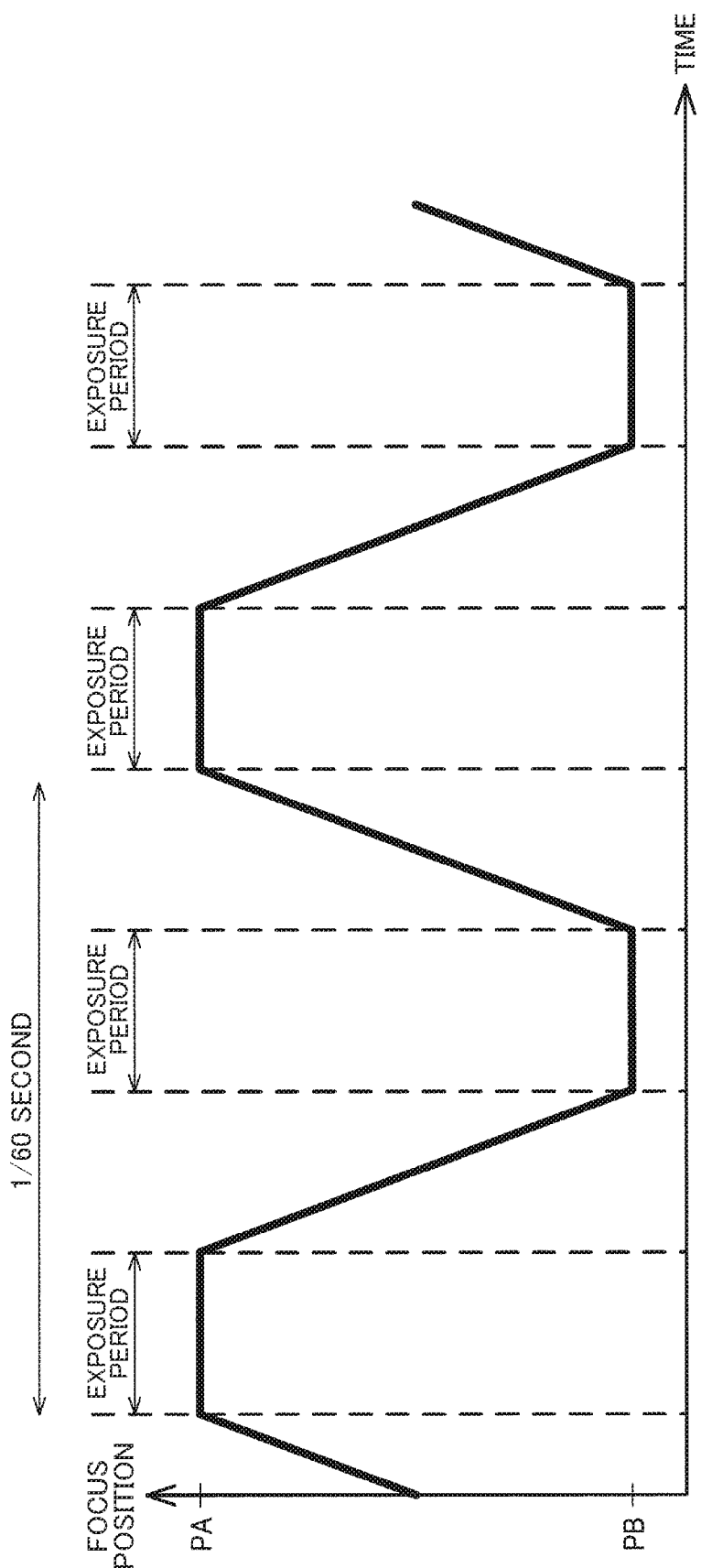
FIG. 6 is a graph of a first example of a change pattern of a focus position.

FIG. 6 is a graph of a first example of a change pattern of the focus position. In this example, the focus position is changed to show a trapezoidal shape and is stopped during the exposure period.

Specifically, the focus position is stopped at a focus position PA during a first exposure period and at a focus position PB during a subsequent second exposure period. The focus position is moved (e.g., linearly at a constant speed) in a period other than the exposure period. This operation is performed in 1/60 second and is repeated every 1/60 second.

Performing imaging in the first exposure period and the second exposure period with the focus position stopped can suppress deterioration in image quality caused by a change in the focus position during imaging. In addition, changing the focus position in a cycle of 1/60 second allows acquiring two images captured at different focus positions every 1/60 second (i.e., acquiring the depth of field extended image of 60 fps).

Figure 7:
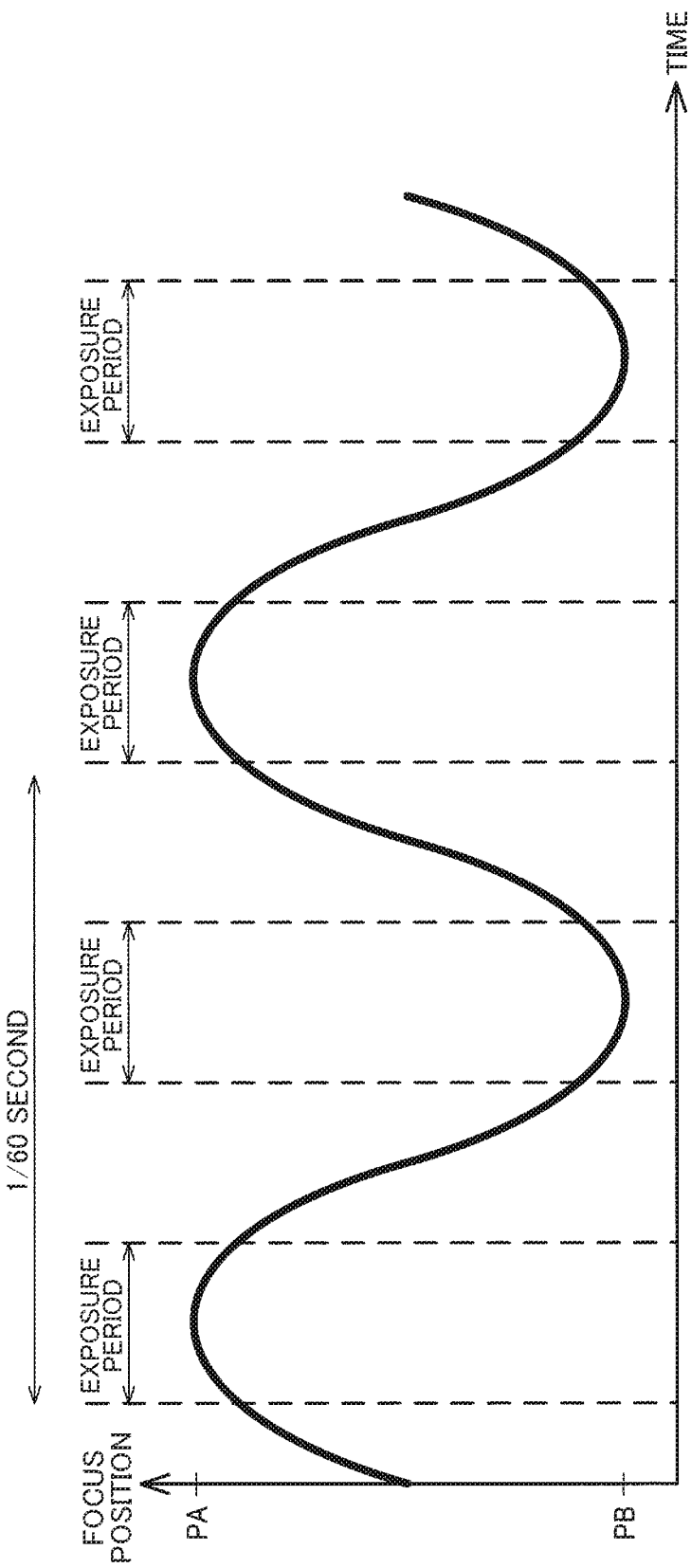
FIG. 7 is a graph of a second example of a change pattern of a focus position.

FIG. 7 is a graph of a second example of the change pattern of the focus position. In this example, the focus position is changed to show a sine wave shape and the exposure period includes the stop timing of the focus position.

Specifically, the focus position is changed to show a sine wave shape with a focus position PA and a focus position PB as apexes (extreme points). The first exposure period includes the apex at the focus position PA and the subsequent second exposure period includes the apex at the focus position PB. The cycle of the sine wave is 1/60 second.

It is known that high driving acceleration (quick acceleration and deceleration) of an actuator shortens a lifespan (a service life) of the actuator. Changing the focus position to show a smooth waveform like the sine wave reduces the driving acceleration (makes the acceleration and deceleration gentle) of the actuator and thus suppresses aged deterioration of the actuator. In addition, changing the focus position to show the sine wave in a cycle of 1/60 second allows acquiring two images captured at different focus positions every 1/60 second.

Figure 8:
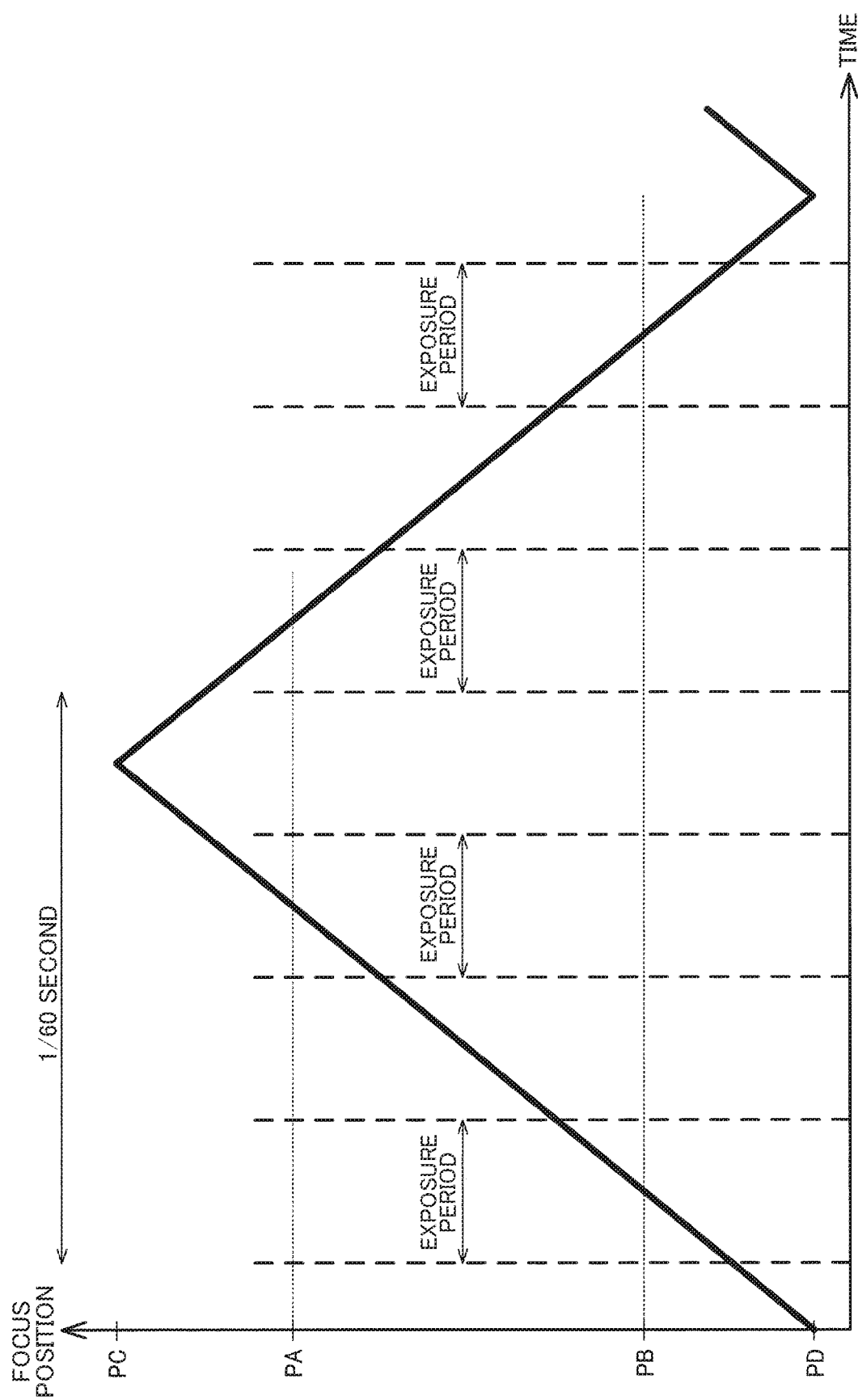
FIG. 8 is a graph of a third example of a change pattern of a focus position.

FIG. 8 is a graph of a third example of the change pattern of the focus position. In this example, the focus position is changed in a cycle of 1/30 second and is moved in an order of focus positions PB, PA, PA, and PB every 1/30 second.

Specifically, the focus position is reciprocated between a focus position PC on a far point side of the focus position PA and a focus position PD on a near side point of the focus position PB in a cycle of 1/30 second. A first exposure period includes a timing when the focus position is at the focus position PB, a subsequent second exposure period includes a timing when the focus position is at the focus position PA, a subsequent third exposure period includes a timing when the focus position is at the focus position PA, and a subsequent fourth exposure period includes a timing when the focus position is at the focus position PB. For example, the centers of the first exposure period and the fourth exposure period coincide with the timings when the focus position is at the focus position PB, and the centers of the second exposure period and the third exposure period coincide with the timings when the focus position is at the focus position PA. The images captured in the first exposure period and the second exposure period are combined into a depth of field extended image, and the images captured in the third exposure period and the fourth exposure period are combined into another depth of field extended image. Although the focus position is moved to show a straight line in FIG. 8, the present disclosure is not limited to this. For example, the focus position may be moved to show the sine wave in a cycle of 1/30 second.

Changing the focus position in a cycle of 1/30 second allows reducing the maximum speed required of the actuator. This configuration can suppress aged deterioration of the actuator. In addition, changing the focus position in the order of the focus positions PB, PA, PA, and PB allows acquiring two images captured at different focus positions PA and PB every 1/60 second.

Figure 9:
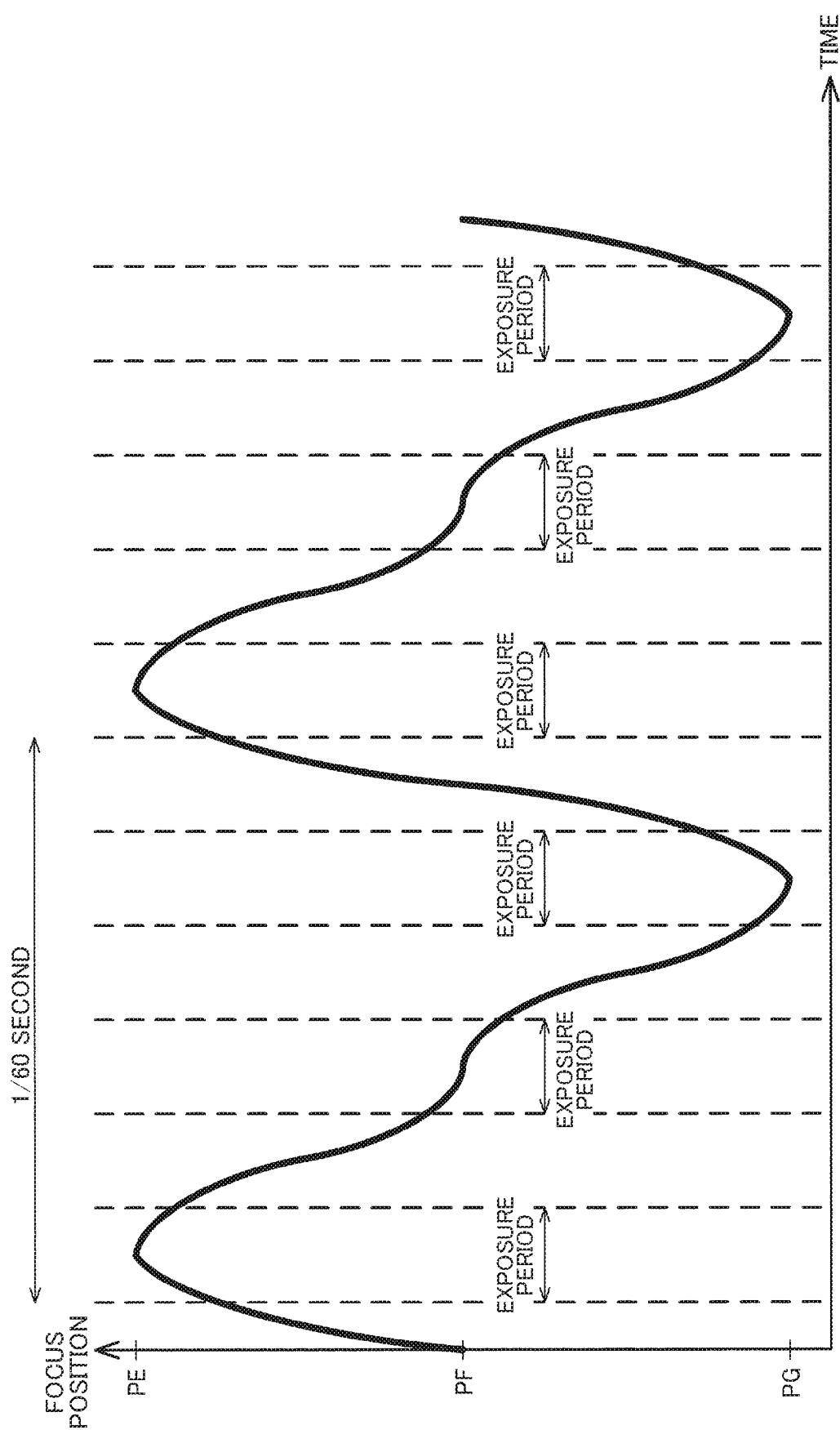
FIG. 9 is a graph of a fourth example of a change pattern of a focus position.

FIG. 9 is a graph of a fourth example of the change pattern of the focus position. In this example, three stop timings of the focus position exist in 1/60 second, and imaging is performed in the exposure periods including these stop timings. That is, imaging is performed at 180 fps.

Specifically, the focus position is reciprocated between a focus position PE on a far point side and a focus position PG on a near point side in a cycle of 1/60 second. The focus position is stopped at a focus position PF on the way from the focus position PE to the focus position PG. An inclination of a change in the focus position at the focus position PF is zero. The focus position PF is a focus position between the focus positions PE and the focus position PG, and, for example, is the center between the focus position PE and the focus position PG. The focus position is changed to show a smooth waveform. A first exposure period includes a timing when the focus position is at the focus position PE, a subsequent second exposure period includes a timing when the focus position is at the focus position PF, and a subsequent third exposure period includes a timing when the focus position is at the focus position PG, For example, the center of the first exposure period is the timing when the focus position is at the focus position PE, the center of the second exposure period is at the timing when the focus position is at the focus position PF, and the center of the third exposure period is at the timing when the focus position is at the focus position PG. Three images captured in the first to third exposure periods are combined into a depth of field extended image.

Since three stop timings of the focus position exist in 1/60 second, three images captured at different focus positions can be acquired every 1/60 second. That is, the depth of field extended image of 60 fps is acquired. This configuration can extend the depth of field three times as deep as the depth of field of each image before the combination. In addition, changing the focus position to show a smooth waveform can suppress aged deterioration of the actuator.

In the examples in FIGS. 5 to 9 described above, two or three frames of images are captured at different focus positions and are combined into the depth of field extended image in one frame. However, the present disclosure is not limited to this. That is, it is only needed to acquire two or more frames (N frames) captured at different focus positions and combine them into the depth of field extended image in one frame. In addition, in the examples in FIGS. 5 to 9, the images in N frames are captured in 1/60 second (at N*60 fps) to generate the depth of field extended image of 60 fps. However, the present disclosure is not limited to this. For example, the images in N frames may be captured in 1/30 second (or 1/120 second) to generate a depth of field extended image of 30 fps (or 120 fps).

4. Control of Quantity of Light Emission

FIG. 10 is a graph of a first example of a control method of the quantity of light emission. In this example, the quantity of light emission per unit time is constant and thus the total quantity of light emission is controlled by the length of the light emission period. The total quantity of light emission is a quantity of light emission in one exposure period and is found by integrating time changes in the quantity of light emission with respect to the exposure period. With the constant quantity of light emission per unit time, the total quantity of light emission is found by multiplying the quantity of light emission per unit time by the length of the light emission period.

Specifically, images IA1 and IA2 are combined into a depth of field extended image EIA, and images IB1 and IB2 are combined into another depth of field extended image EIB. In this case, the light emission periods when the images IA1 and IA2 are captured are identical light emission periods TLA, and the light emission periods when the images IB1 and IB2 are captured are identical light emission periods TLB.

Figure 11:
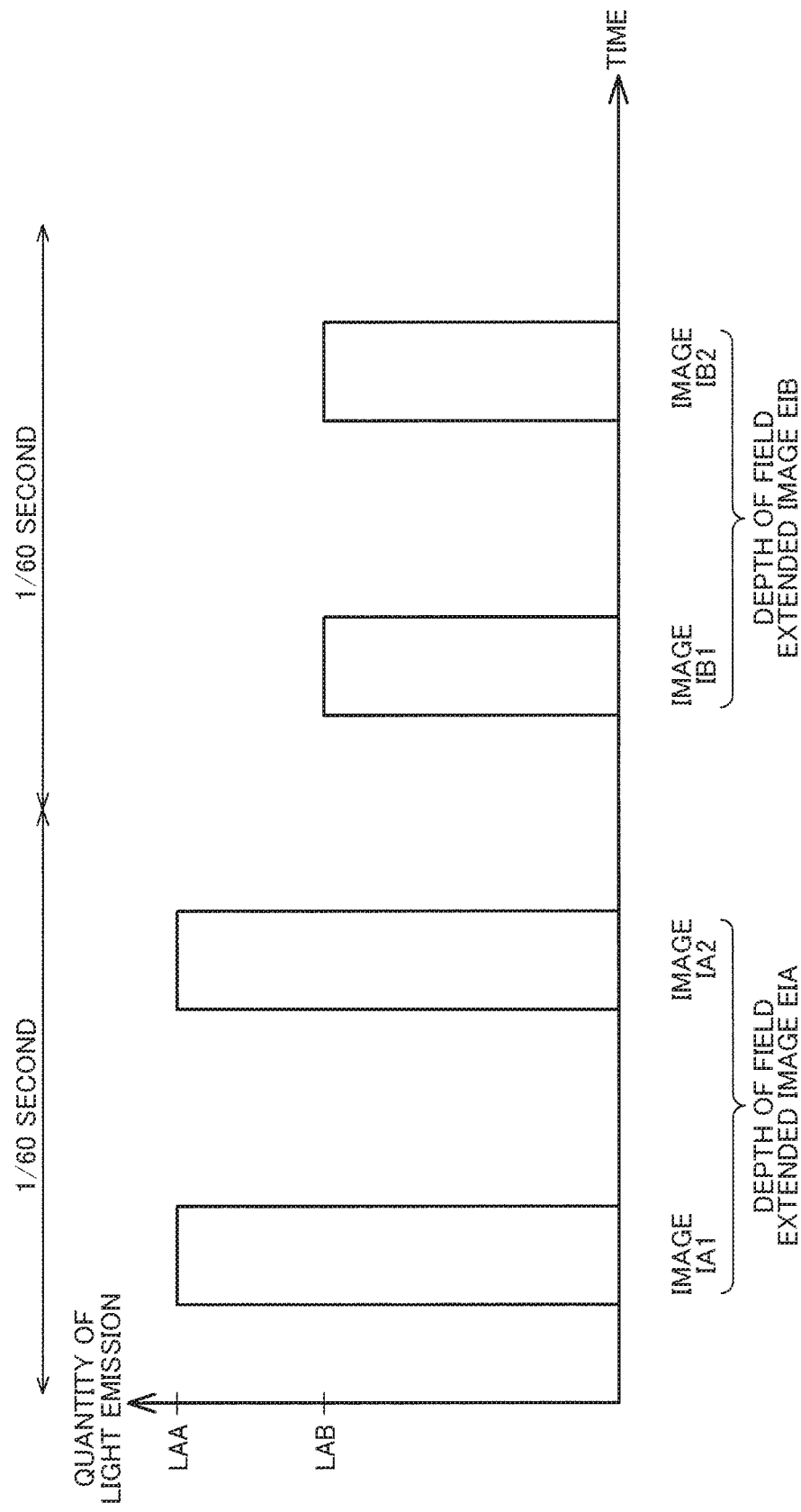
FIG. 11 is a graph of a second example of a control method of a quantity of light emission.

FIG. 11 is a graph of a second example of the control method of the quantity of light emission. In this example, the length of the light emission period is constant and thus the total quantity of light emission is controlled by the quantity of light emission per unit time.

Specifically, the respective quantities of light emission per unit time when the images IA1 and IA2 are captured are identical quantities of light emission LAA, and the respective quantities of light emission per unit time when the images IB1 and IB2 are captured are identical quantities of light emission LAB.

A difference in brightness between the images (e.g., the images IA1 and IA2) to be combined may generate an artifact such as luminance unevenness in the depth of field extended image. This may degrade a quality of an endoscope image. As illustrated in FIGS. 10 and 11, the total quantity of light emission is maintained constant in the respective frames when the images in N frames to be combined into the depth of field extended image in one frame are captured. This configuration can suppress deterioration in the image quality.

In the examples described above, either the quantity of light emission per unit time or the light emission period is controlled. However, the control method of the total quantity of light emission is not limited to this. That is, it is only needed that the respective total quantities of light emission in the exposure periods are equal. The total quantity of light emission is found by integrating the time changes in the quantity of light emission in one exposure period with respect to the exposure period. For example, when a light source that emits pulse light is adopted, the number of light emission in the exposure period may be controlled to control the total quantity of light emission.

5. Synchronous Control

FIG. 12 is a graph illustrating a synchronous control between the focus position and a light emitting timing. In FIG. 12, the focus position is indicated by a thick solid line and the quantity of light emission by a thin solid line. The illumination light is emitted in synchronization with the stop timing of the focus position, as illustrated in FIG. 12.

Specifically, the focus position stops at a focus position PA at timings (time) ta1 and tb1, and at a focus position PB at timings ta2 and tb2. A timing of a center of a light emission period TLA1 is set to coincide with the timing ta1, and a timing of a center of a light emission period TLA2 is set to coincide with the timing ta2. The respective total quantities of light emission in the light emission period TLA1 and the light emission period TLA2 are equal. Similarly, a timing of a center of a light emission period TLB1 is set to coincide with the timing tb1, and a timing of a center of a light emission period TLB2 is set to coincide with the timing tb2. The respective total quantities of light emission in the light emission period TLB1 and the light emission period TLB2 are equal.

Most of the light emitted to the subject in the endoscope image is the illumination light emitted from the illumination section 600. The illumination light is emitted in the exposure period of the image sensor 220 to acquire the subject image. As illustrated in FIG. 12, the illumination light is emitted in synchronization with the stop timings (ta1, ta2, tb1, and tb2) of the focus position, and thus a change in the focus position in the light emission period is reduced. This configuration can suppress deterioration in image quality caused by the change in the focus position during imaging.

Figure 13:
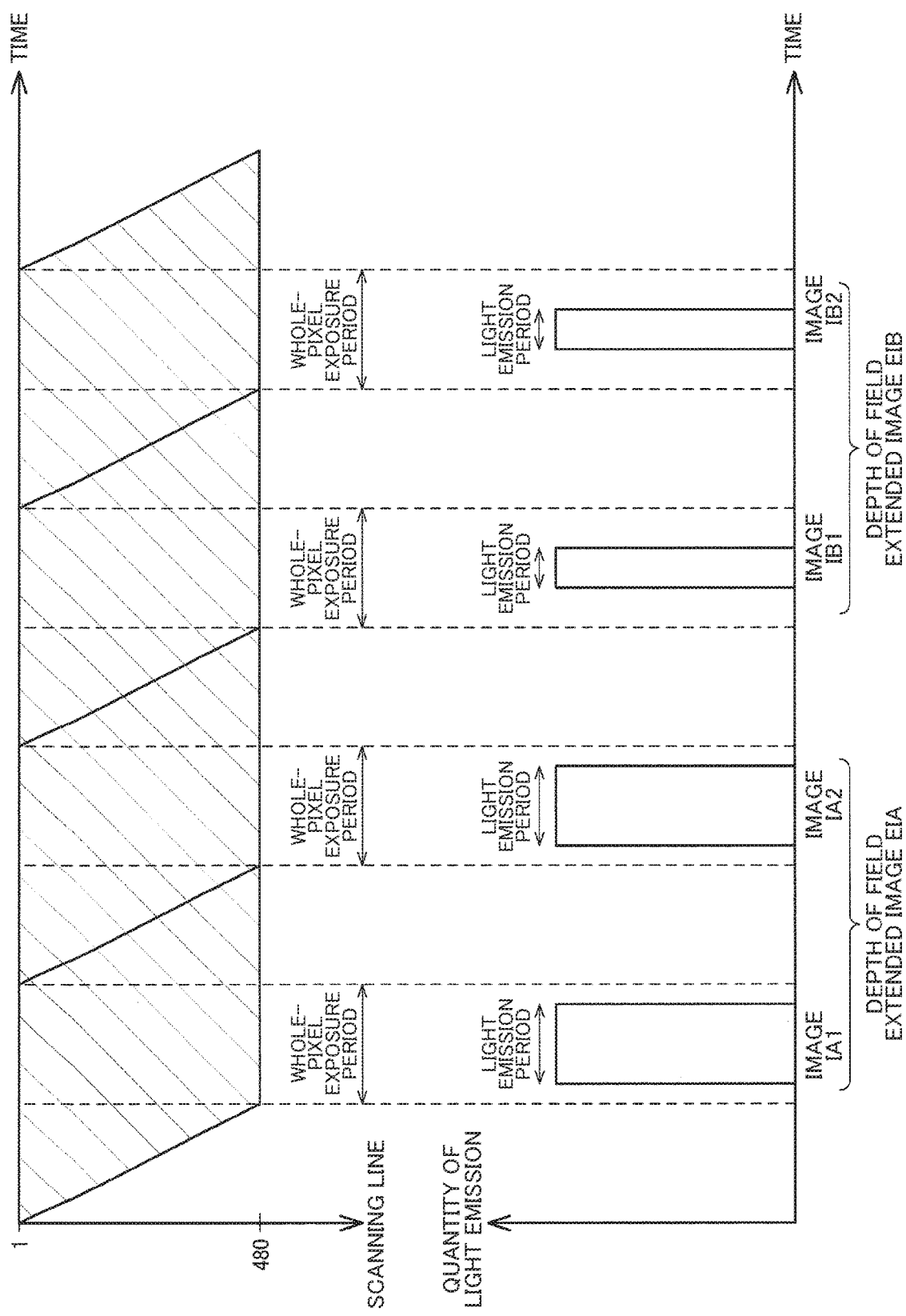
FIG. 13 is a graph illustrating a synchronous control between exposure of an image sensor and light emission by an illumination section.

FIG. 13 is a graph illustrating a synchronous control between the exposure of the image sensor and the light emission by the illumination section. In FIG. 13, the exposure of the image sensor 220 is performed by the rolling shutter system and the light emission period is set in the whole-pixel exposure period. The image sensor 220 described herein includes 480 scanning lines (scanning lines in the effective pixel region). However, the number of scanning lines is not limited to this.

In the rolling shutter system, the exposure of a first scanning line of the image sensor 220 is started and then the exposure of a second scanning line is started. This process is sequentially performed up to a 480th scanning line. After the exposure of the 480th scanning line is started, the exposure of the first scanning line is ended and a pixel value of the first scanning line is read out. Then, the exposure of the second scanning line is ended and the pixel value of the second scanning line is read out. This process is sequentially performed up to the 480th scanning line. All the first to 480th scanning lines are in the exposure state in a period after the exposure of the 480th scanning line is started and before the exposure of the first scanning line is ended. This period is called as the whole-pixel exposure period.

The light emission period is set in the whole-pixel exposure period. That is, the length of the light emission period is shorter than the length of the whole-pixel exposure period, and the light emission period starts after a start of the whole-pixel exposure period and ends before an end of the whole-pixel exposure period. The light emission period is preferably set such that the center of the whole-pixel exposure period coincides with the center of the light emission period. As described referring to FIG. 12, the focus position is synchronized such that the stop timing of the focus position is in the light emission period.

The rolling shutter system sequentially exposes the scanning lines and thus generates a phenomenon that a subject image is distorted due to a movement of the subject (so-called rolling shutter distortion). The endoscope apparatus captures the image of the subject on which the illumination light is emitted. Thus, the rolling shutter distortion is generated when the illumination light is emitted at a timing when both the scanning line in the exposure period and the scanning line out of the exposure period exist. As illustrated in FIG. 13, the illumination light is emitted in the whole-pixel exposure period, and thus generation of the rolling shutter distortion can be prevented.

Figure 14:
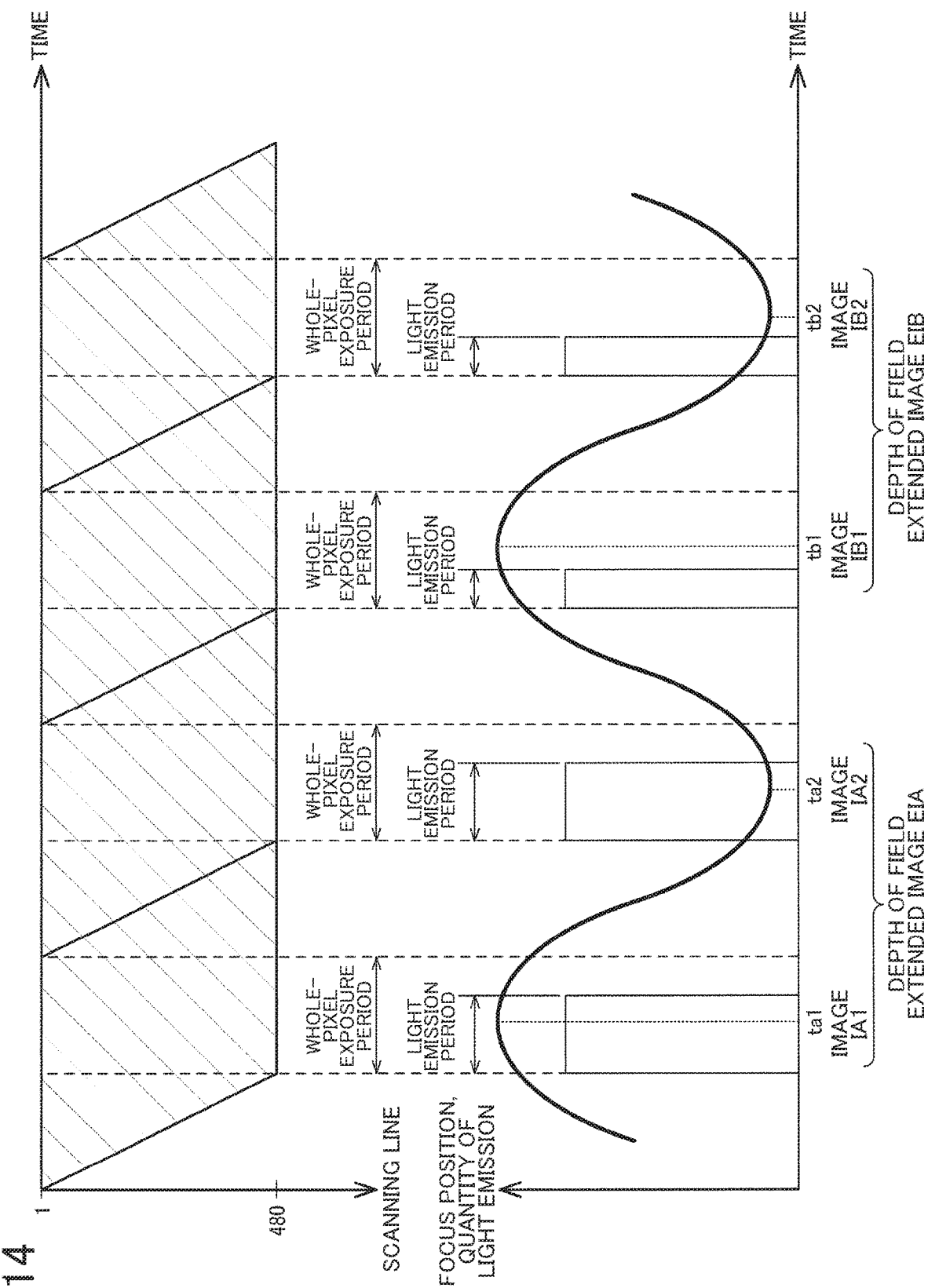
FIG. 14 is a graph illustrating an operation when a center of a light emission period does not coincide with a stop timing of the focus position.

As illustrated in FIG. 14, when the center of the light emission period does not coincide with the stop timing of the focus position, the stop timing of the focus position may be out of the light emission period. For example, such a situation may be created when the total quantity of light emission is controlled by the length of the light emission period. Adjusting the phase of the change in the focus position in accordance with the length of the light emission period can make the stop timing of the focus position be in the light emission period. However, this complicates the focus position control. In FIG. 13, the center of the whole-pixel exposure period is made to coincide with the center of the light emission period. As a result, the stop timing of the focus position can be in the light emission period even when the length of the light emission period changes. For example, the center of the whole-pixel exposure period, the center of the light emission period, and the stop timing of the focus position are made to coincide one another. In addition, waveforms of the changes in the focus position can be made identical in respective cycles, regardless of the length of the light emission period.

In addition, assume that the center of the light emission period is made to coincide with the stop timing of the focus position. When the center of the whole-pixel exposure period does not coincide (synchronize) with the stop timing of the focus position, a maximum length of the light emission period becomes shorter than the length of the whole-pixel exposure period. In FIG. 13, the center of the whole-pixel exposure period, the center of the light emission period, and the stop timing of the focus position are made to coincide, and thus the maximum length of the light emission period is equal to the length of the whole-pixel exposure period. This configuration can maximize a maximum total quantity of light emission.

Figure 15:
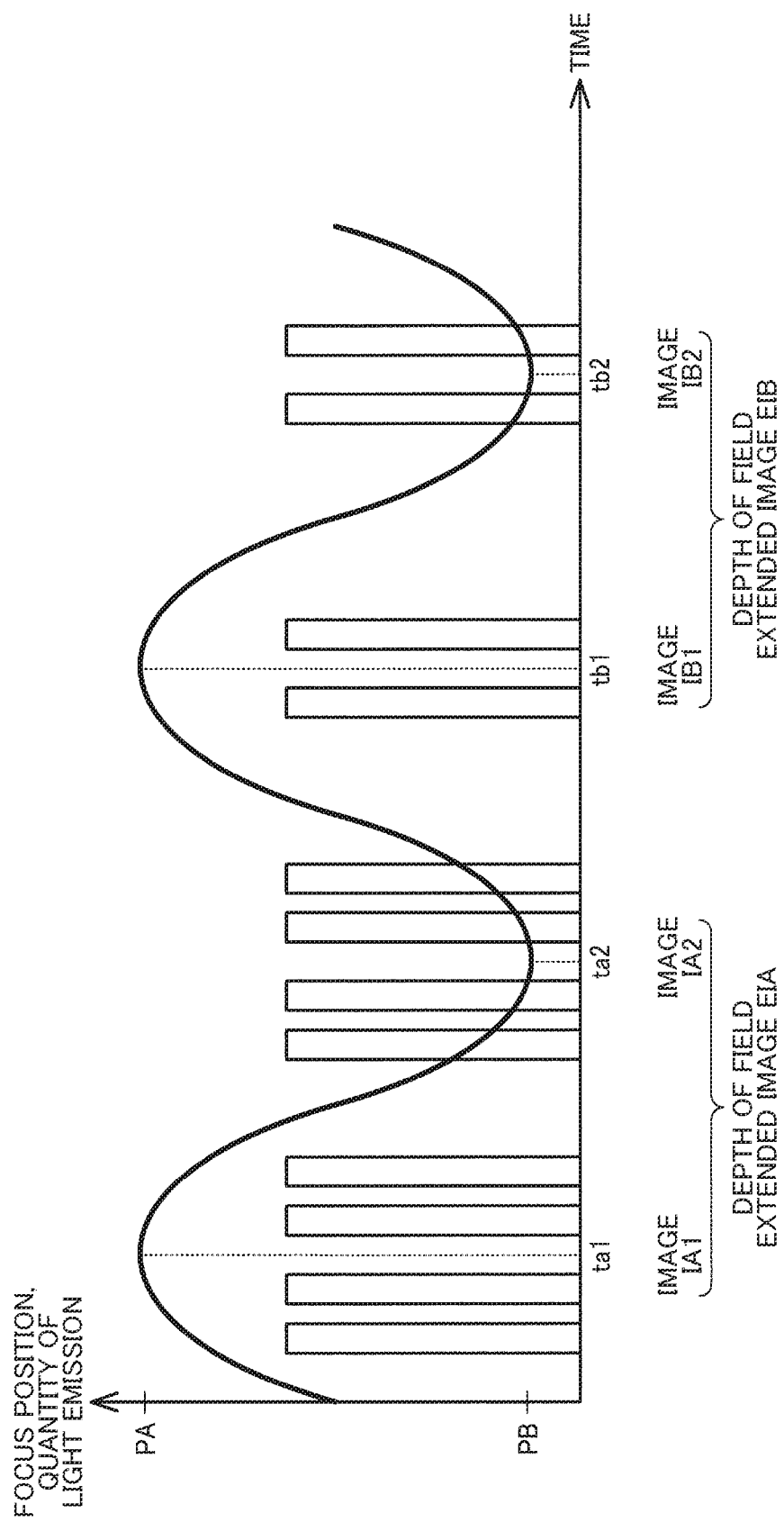
FIG. 15 is a graph illustrating a synchronous control between the focus position and the light emitting timing when pulse light emission is performed.

FIG. 15 is a graph illustrating a synchronous control between the focus position and the light emitting timing when the pulse light emission is performed. In FIG. 15, the focus position is indicated by a thick solid line and the quantity of light emission by a thin solid line. As illustrated in FIG. 15, the stop timing of the focus position is made to coincide with the gravity center of the total quantity of light emission of the pulse light emission.

Specifically, assume that a quantity of light emission of one pulse is a quantity HR and an emitting timing of this pulse is a timing t. The quantity HR may differ for each pulse. In this case, a timing when a value found by integrating the quantities HR of all pulses in a relation of t<tgc in the exposure period is equal to a value found by integrating the quantities HR of all pulses in a relation of t>tgc in the exposure period corresponds to the gravity center of the total quantity of light emission. It is only needed to make this timing coincide with the stop timing of the focus position.

For example, the pulse light emission is performed four times with equal quantities of light emission at symmetric timings with respect to a timing ta1 when the focus position is at a focus position PA in an exposure period of an image IA1. In this case, the pulse light emission is performed twice each before and after the timing ta1. As for the pulse light emission in exposure periods of images IA2, IB1, and IB2, the numbers of pulse light emission are equal before and after the stop timing of the focus position.

As described above, the stop timing of the focus position is made to coincide with the gravity center (or the center) of the total quantity of light emission of the pulse light emission, and thus the focus position and the timing of the pulse light emission can be appropriately synchronized. That is, the image can be acquired at a desired focus position (a position where the focus position is stopped) regardless of the number of light emission or the quantity of light emission of each pulse.

In the examples in FIGS. 5 to 15, the control for making the brightness of the images in N frames to be combined into the depth of field extended image constant is implemented by the control of the illumination light. However, the present disclosure is not limited to this. For example, the brightness of the captured images may be corrected by the image processing to make the brightness of the images in N frames to be combined into the depth of field extended image constant. Alternatively, a method for controlling the illumination light and a method for correcting the brightness of the images by the image processing may be combined to make the brightness of the images in N frames to be combined into the depth of field extended image constant. Details of the method for correcting the brightness of the images by the image processing will be described later.

6. Combining Method Into Depth of Field Extended Image

Figure 16:
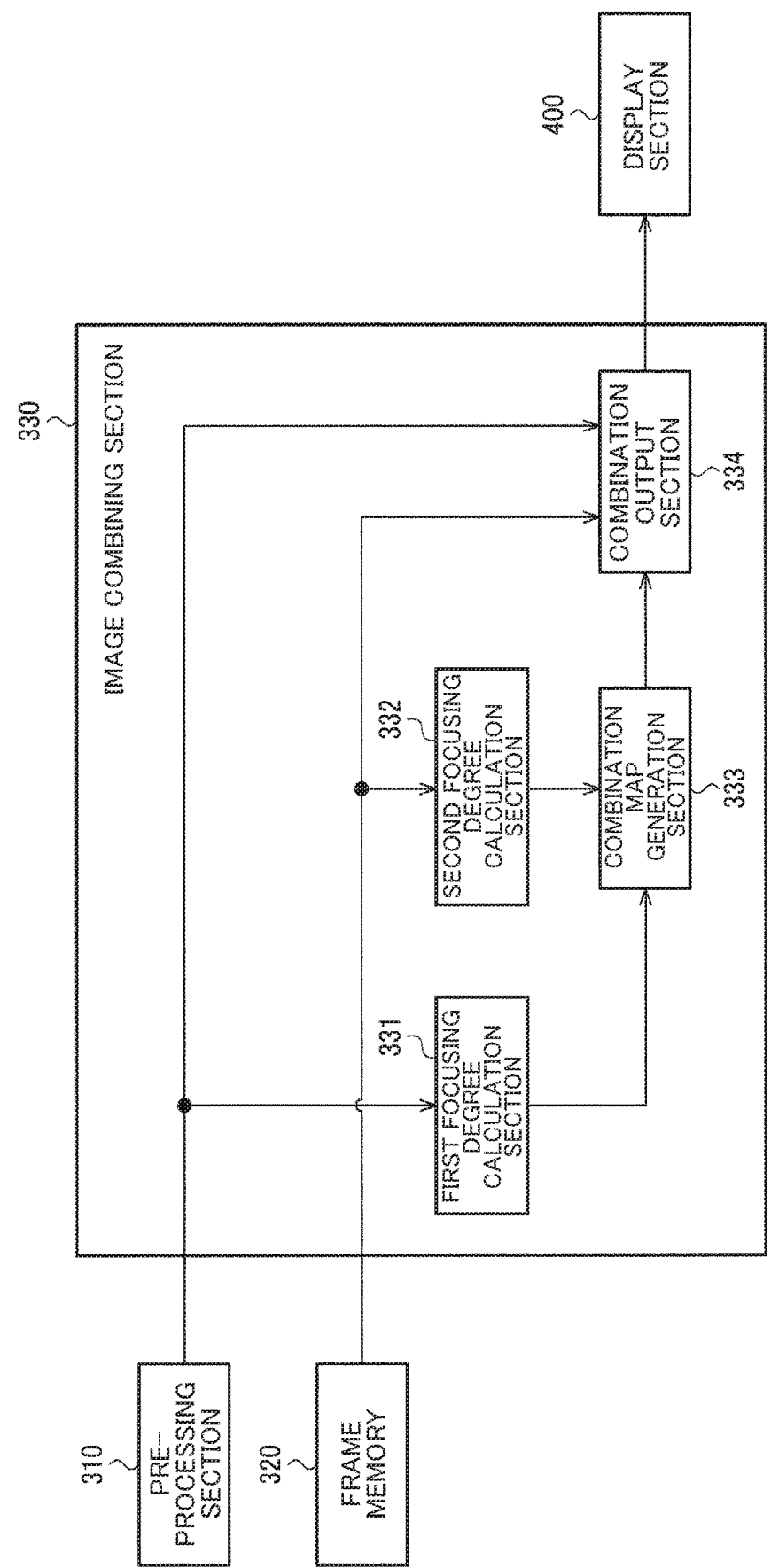
FIG. 16 is a diagram illustrating a detailed configuration example of an image combining section.

FIG. 16 is a diagram illustrating a detailed configuration example of the image combining section 330. The image combining section 330 includes a first focusing degree calculation section 331, a second focusing degree calculation section 332, a combination map generation section 333, and a combination output section 334.

The first focusing degree calculation section 331 calculates a focusing degree of each pixel in the image output from the preprocessing section 310. Specifically, the first focusing degree calculation section 331 performs a filter process e.g., a high pass filter process or a bandpass filter process) on the image and outputs a process result as the focusing degree. The first focusing degree calculation section 331 outputs the calculated focusing degree to the combination map generation section 333 as a first focusing degree.

The second focusing degree calculation section 332 calculates the focusing degree of each pixel in the image stored in the frame memory section 320. For example, the second focusing degree calculation section 332 performs the high pass filter process or the bandpass filter process on the image and outputs a process result as the focusing degree. The second focusing degree calculation section 332 outputs the calculated focusing degree to the combination map generation section 333 as a second focusing degree.

The combination map generation section 333 compares the first focusing degree with the second focusing degree of each pixel, and generates a combination map equal in size to the image based on comparison results. The combination map is a map storing "1" or "0" in each pixel. For example, when the first focusing degree of a certain pixel is higher than the second focusing degree of that pixel, a value "1" is stored in the pixel. When the first focusing degree of the pixel is equal to or lower than the second focusing degree of the pixel, a value "0" is stored in the pixel.

The combination output section 334 selects a pixel of either the image output from the preprocessing section 310 or the image stored in the frame memory section 320 based on the value in the combination map, and outputs an image including the selected pixels as a depth of field extended image. The combination output section 334 selects a pixel value of the image output from the preprocessing section 310 when the value of the pixel in the combination map is "1", and selects a pixel value of the image stored in the frame memory section 320 when the value of the pixel in the combination map is "0".

In the example described above, the pixel value of one of the images in N frames is selected. However, the combining method into the depth of field extended image is not limited to this. For example, the combination map may be multi-valued (store a blend ratio in each pixel) based on a high-low relationship between the first focusing degree and the second focusing degree, and the pixel values of the image output from the preprocessing section 310 and the image stored in the frame memory section 320 may be blended to output the depth of field extended image.

More preferably, the image combining section 330 includes a positioning section (not illustrated) and the positioning section performs positioning of each pixel in the image stored in the frame memory section 320 based on the image output from the preprocessing section 310. Then, the combination output section 334 combines the image output from the preprocessing section 310 and a resultant image of the positioning into the depth of field extended image.

7. Method of Brightness Correction by Image Processing

Figure 17:
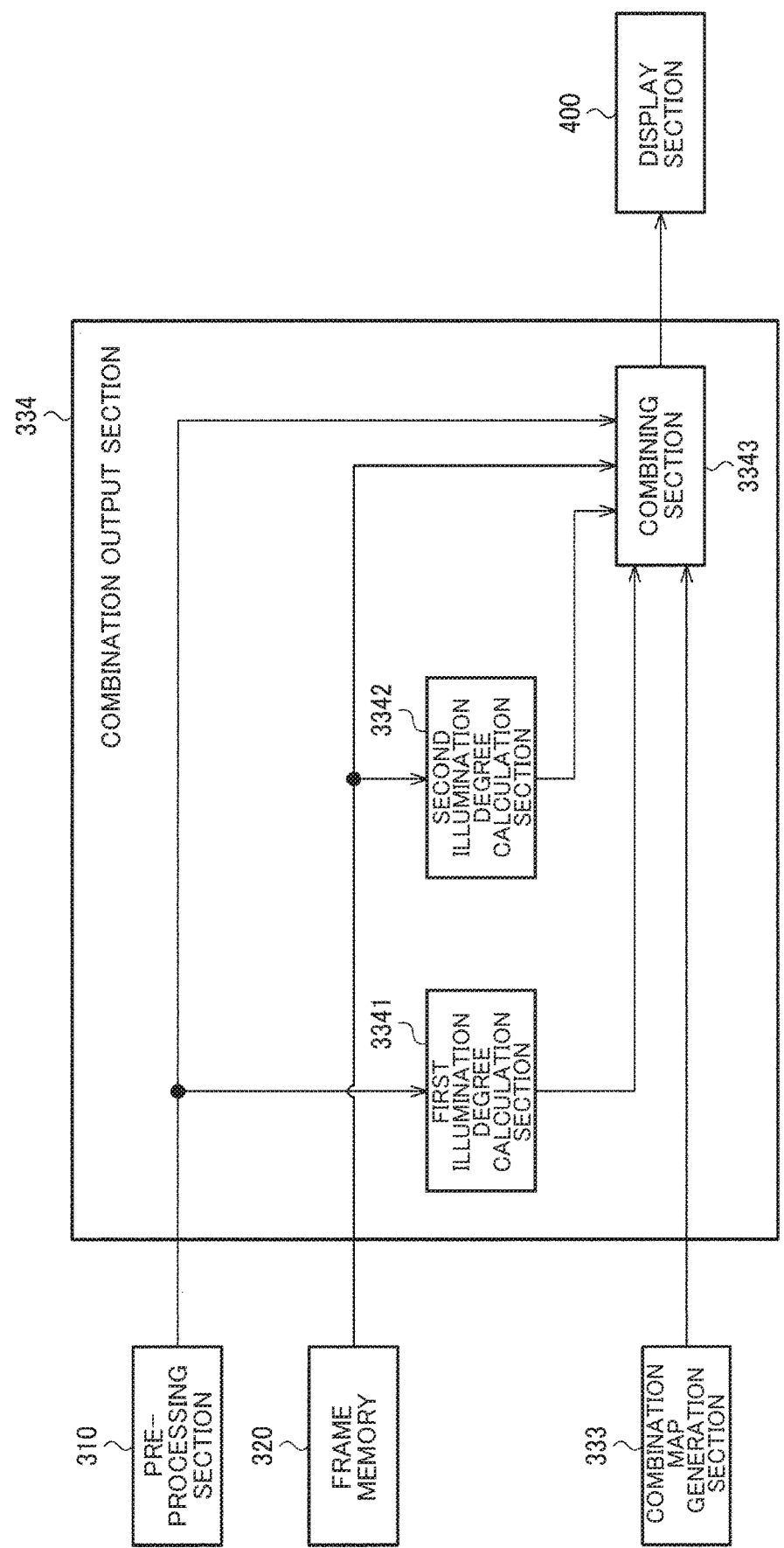
FIG. 17 is a diagram illustrating a detailed configuration example of a combination output section when brightness correction is performed by image processing.

FIG. 17 is a diagram illustrating a detailed configuration example of the combination output section 334 when the brightness correction is performed by the image processing. The combination output section 334 includes a first illumination degree calculation section 3341, a second illumination degree calculation section 3342, and a combining section 3343.

The first illumination degree calculation section 3341 calculates an illumination degree of each pixel in the image output from the preprocessing section 310. The illumination degree is an index that indicates local brightness of the image. For example, the first illumination degree calculation section 3341 performs a low pass filter process or the bandpass filter process on the image and outputs a process result as the illumination degree. The first illumination degree calculation section 3341 outputs the calculated illumination degree to the combining section 3343 as a first illumination degree.

The second illumination degree calculation section 3342 calculates the illumination degree of each pixel in the image stored in the frame memory section 320. For example, the second illumination degree calculation section 3342 performs the low pass filter process or the bandpass filter process on the image and outputs a process result as the illumination degree. The second illumination degree calculation section 3342 outputs the calculated illumination degree to the combining section 3343 as a second illumination degree.

The combining section 3343 selects a pixel of either the image output from the preprocessing section 310 or the image stored in the frame memory section 320 based on the value in the combination map, and outputs an image including the selected pixels as a depth of field extended image. At this time, the combining section 3343 corrects a pixel value I of the image stored in the frame memory section 320 based on a first illumination degree B1 and a second illumination degree B2, and selects a corrected pixel value I'. For example, the pixel value is corrected by the following Formulas 1 and 2.

[Formula 1]
$$I' = \frac{B1}{B2} \times I \quad (1)$$

[Formula 2]
$$I' = I - B2 + B1 \quad (2)$$

8. Method of Light Adjustment Control

Figure 18:
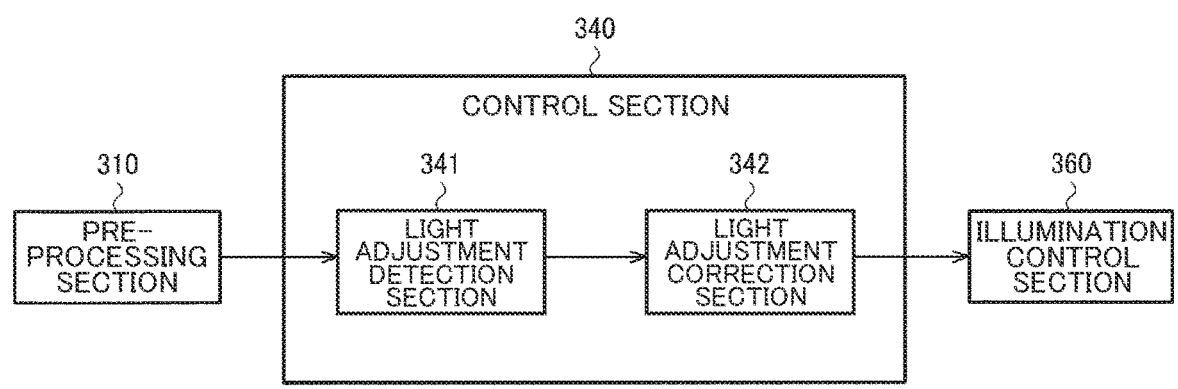
FIG. 18 is a diagram illustrating a detailed configuration example of a control section.

A method of a light adjustment control is described below. FIG. 18 is a detailed configuration example of the control section 340. The control section 340 includes a light adjustment detection section 341 and a light adjustment correction section 342.

The light adjustment detection section 341 calculates a light adjustment detection value from the pixel value of the image output from the preprocessing section 310. For example, the light adjustment detection section 341 outputs an average value found by averaging luminance signals of respective pixels by all pixels as the light adjustment detection value. The light adjustment detection section 341 outputs the light adjustment detection value to the light adjustment correction section 342. The average value of the luminance signals may be calculated only in a central part of the image. Alternatively, the average value of the luminance signals may be calculated by sampling the luminance signals at intervals of an appropriate number of pixels to reduce a calculation load.

The light adjustment correction section 342 calculates an illumination correction coefficient C based on a light adjustment detection value D output from the light adjustment detection section 341 and a predetermined light adjustment criterion value S. For example, the illumination correction coefficient is calculated by the following Formula 3. The light adjustment correction section 342 outputs the illumination correction coefficient to the illumination control section 360.

[Formula 3]
$$C = \frac{S}{D} \quad (3)$$

The illumination light control section 360 controls a quantity $E_1$ of light emission of the illumination light at a timing subsequent to a current timing with respect to a quantity $E_0$ of light emission of the illumination light at the current tuning by the following Formula 4.

[Formula 4]
$$E_1 = E_0 \times C \quad (4)$$

For example, the quantity $E_0$ of light emission corresponds to the quantity of light emission when the images IA1 and IA2 in FIGS. 10, 11, and 15 are captured (the total quantity of light emission in the exposure period), and the quantity $E_1$ of light emission corresponds to the quantity of light emission when the images IB1 and IB2 in FIGS. 10, 11, and 15 are captured (the total quantity of light emission in the exposure period). The illumination correction coefficient C for controlling the quantity of light emission $E_1$ is calculated based on at least one of the images IA1 and IA2.

In the example described above, the light adjustment detection section 341 calculates the light adjustment detection value from the pixel value of the image output from the preprocessing section 310. However, the light adjustment detection section 341 may calculate the light adjustment detection value from the depth of field extended image output from the image combining section 330. Specifically, the light adjustment detection section 341 calculates the light adjustment detection value from the depth of field extended image EIA in FIGS. 10, 11, and 15, and the light adjustment correction section 342 calculates the illumination correction coefficient. Then, the illumination control section 360 controls the quantity of light emission when the images IB1 and IB2 are captured.

In addition, in FIGS. 10, 11, and 15, the depths of field of the images IA1 and IA2, the images IA2 and IB1, and the images IB1 and IB2 may be sequentially combined. In this case, the quantity of light emission when the image IB1 is captured may be calculated from the depth of field extended image combining the images IA1 and IA2, and the quantity of light emission when the image IB2 is captured may be calculated from the depth of field extended image combining the images IA2 and IB1. When the quantities of light emission when two images to be combined are captured are different, the brightness correction by the image processing described above is performed to combine the images into the depth of field extended image.

9. Surgery Support System

The endoscope apparatus (an endoscope system) in accordance with the present embodiment is assumed to be a type in which the insertion section (the scope) is connected to the control device (the processing section) to allow the user to operate the scope to photograph the inside of a body as illustrated in FIG. 4, for example. However, the present disclosure is not limited to this. As an endoscope apparatus applied with the present disclosure, a surgery support system using a robot can be assumed, for example.

Figure 19:
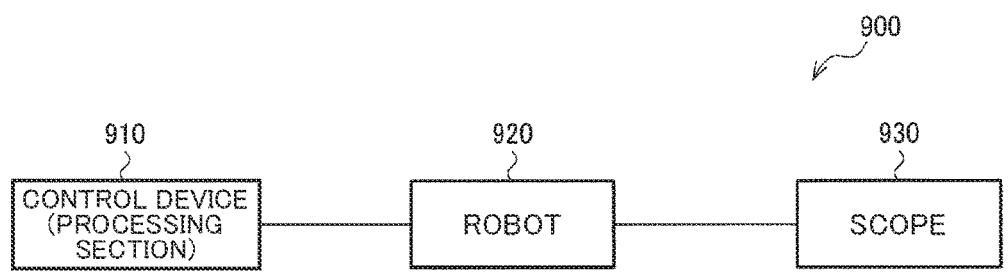
FIG. 19 is a diagram illustrating a configuration example of a surgery support system.

FIG. 19 illustrates a configuration example of the surgery support system. A surgery support system 900 includes a control device 910 (the processing section), a robot 920 (a robot main body), and a scope 930 (e.g., a rigid scope). The control device 910 is a device that controls the robot 920. That is, the user operates an operation section of the control device 910 to move the robot through which to perform surgery on a patient. In addition, the user operates the operation section of the control device 910 to manipulate the scope 930 via the robot 920 and photograph a surgical region. The control device 910 includes the processing section 300 in FIG. 1 or 4. The user operates the robot while seeing the images displayed on a display device (not illustrated) by the processing section 300, The present disclosure can be applied to the control device 910 in such a surgery support, system 900. The control device 910 may be integrally configured with (be embedded in) the robot 920, or be disposed outside the robot 920 as a separate device.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
a processor configured to:
control a focus position of an objective optical system, the objective optical system being configured to form an image of reflected light from a subject on an image sensor, the subject reflecting illumination light emitted thereon, such that focus positions at timings when respective images in N frames are sequentially captured by the image sensor differ from each other, N being an integer of two or more;
control a quantity of light emission of the illumination light such that quantities of light emission of the illumination light when the respective images in N frames are captured become equal to each other, or performing a correction process of at least one of the respective images such that brightness of the respective images in N frames becomes equal to each other; and
after controlling the focus position and controlling the quantities of light emission or performing the correction process, combine the respective images in N frames, each having different focused parts, into a depth of field extended image in one frame by coupling the focused parts with each other.

2. The endoscope apparatus as defined in claim 1, wherein the processor is configured to control the illumination light to adjust brightness of the depth of field extended image, and maintain the quantity of light emission to be constant when the respective images in N frames are captured.

3. The endoscope apparatus as defined in claim 2, wherein the processor is configured to control emission of the illumination light in a light emission period including a stop timing of the focus position.

4. The endoscope apparatus as defined in claim 2, wherein the processor is configured to:
control the focus position to reciprocate the focus position between a first focus position and a second focus position that differs from the first focus position;
control emission of the illumination light in a first light emission period including a timing when the focus position is at the first focus position and in a second light emission period including a timing when the focus position is at the second focus position; and combine the respective images in N frames including an image captured in the first light emission period and an image captured in the second light emission period into the depth of field extended image.

5. The endoscope apparatus as defined in claim 2,
wherein the image sensor is configured to capture the respective images in N frames by a rolling shutter system, and
wherein the processor is configured to control emission of the illumination light in a whole-pixel exposure period when all lines in an effective pixel region of the image sensor are in an exposure state.

6. The endoscope apparatus as defined in claim 2,
wherein the processor is configured to control a length of a light emission period of the illumination light to control a total quantity of light emission when each of the respective images in N frames is captured.

7. The endoscope apparatus as defined in claim 2,
wherein the processor is configured to control a quantity of light emission of the illumination light per unit time to control a total quantity of light emission when each of the respective images in N frames is captured.

8. The endoscope apparatus as defined in claim 2,
wherein the processor is configured to control emission of the illumination light in a light emission period when a center of an exposure period of the image sensor coincides with a center of the light emission period.

9. The endoscope apparatus as defined in claim 2,
wherein the processor is configured to:
control emission of the illumination light by pulse light emission a plurality of times in an exposure period of the image sensor,
wherein a gravity center of a total quantity of light emission of the pulse light emission coincides with a stop timing of the focus position, and
wherein the gravity center is a timing when a total quantity of light emission of the pulse light emission before the stop timing of the focus position coincides with a total quantity of light emission of the pulse light emission after the stop timing of the focus position.

10. The endoscope apparatus as defined in claim 2,
wherein the processor is configured to:
combine images in a first set of N frames into a first depth of field extended image and images in a second set of N frames captured after the images in the first set of N frames into a second depth of field extended image; and
change the quantity of light emission of the illumination light in a period between a period when the images in the first set of N frames are captured and a period when the images in the second set of N frames are captured.

11. The endoscope apparatus as defined in claim 1,
wherein the processor is configured to:
control emission of the illumination light to adjust brightness of the respective images in N frames captured by the image sensor; and
perform the correction process to make the brightness of the respective images in N frames constant, and combine the images in N frames that have undergone the correction process into the depth of field extended image.

12. The endoscope apparatus as defined in claim 1, comprising:
an illumination device configured to emit the illumination light to the subject; and
an imaging device comprising the objective optical system and the image sensor.

13. An operating method of an endoscope apparatus comprising:
controlling a focus position of an objective optical system, the objective optical system being configured to form an image of reflected light from a subject on an image sensor, the subject reflecting illumination light emitted thereon, such that focus positions at timings when respective images in N frames are sequentially captured by the image sensor differ from each other, N being an integer of two or more;
controlling a quantity of light emission of the illumination light such that quantities of light emission of the illumination light when the respective images in N frames are captured become equal to each other, or performing a correction process of at least one of the respective images such that brightness of the respective images in N frames becomes equal to each other; and
after controlling the focus position and controlling the quantities of light emission or performing the correction process, combining the respective images in N frames, each having different focused parts, into a depth of field extended image in one frame by coupling the focused parts with each other.

14. An endoscope system comprising:
an endoscope comprising an image sensor; and
an endoscope apparatus comprising:
a processor configured to:
control a focus position of an objective optical system;
acquire images sequentially captured by the image sensor;
combine the images in N frames (N is an integer of two or more) each having different focused parts thus acquired into a depth of field extended image in one frame, by coupling the focused parts with each other; and
control the illumination light before combination into the depth of field extended image in one frame;
control the focus position such that focus positions at timings when the respective images in N frames are captured differ from each other;
combine images in a first set of N frames into a first depth of field extended image and images in a second set of N frames captured after the images in the first set of N frames into a second depth of field extended image; and
change a quantity of light emission of the illumination light in a period between a period when the images in the first set of N frames are captured and a period when the images in the second set of N frames are captured, or
perform, before combination into the depth of field extended image in one frame, a correcting process of at least one of the respective images to equalize brightness of the respective images in N frames.

15. The endoscope apparatus as defined in claim 1,
wherein the image sensor is configured to acquire the images at a first focus position and a second focus position that differs from the first focus position.

16. The endoscope apparatus as defined in claim 15,
wherein the first focus position is on a far point side of the second focus position.

* * * * *